United States Patent
Nakanishi et al.

(10) Patent No.: US 8,293,212 B2
(45) Date of Patent: Oct. 23, 2012

(54) INHIBITOR SCREENING METHOD AND ATOPIC DERMATITIS LIKE SYMPTOM INDUCING METHOD WHICH UTILIZES INDUCTION OF PRODUCTION OF INTERLEUKIN 18 BY KERATINOCYTE AND UTILIZATION OF SAME

(75) Inventors: Kenji Nakanishi, Hyogo (JP); Hitoshi Mizutani, Mie (JP); Hiroko Tsutsui, Osaka (JP)

(73) Assignee: Japan Science & Technology Agency, Kawaguchi (JP)

( * ) Notice: Subject to any disclaimer, the term of this patent is extended or adjusted under 35 U.S.C. 154(b) by 513 days.

(21) Appl. No.: 12/499,231

(22) Filed: Jul. 8, 2009

(65) Prior Publication Data

US 2010/0003194 A1 Jan. 7, 2010

Related U.S. Application Data

(62) Division of application No. 10/554,301, filed as application No. PCT/JP2004/005747 on Apr. 21, 2004, now abandoned.

(30) Foreign Application Priority Data

Apr. 24, 2003 (JP) ................................ 2003-120630

(51) Int. Cl.
*A61K 49/00* (2006.01)
*G01N 33/53* (2006.01)
(52) U.S. Cl. ...................................... 424/9.2; 435/7.21
(58) Field of Classification Search ........................ None
See application file for complete search history.

(56) References Cited

U.S. PATENT DOCUMENTS

2003/0159163 A1 8/2003 Mizutani

FOREIGN PATENT DOCUMENTS

| | | |
|---|---|---|
| JP | 2003-038063 | 2/2003 |
| WO | WO-01/95710 | 12/2001 |

OTHER PUBLICATIONS

Colin Jamora and Elaine Fuchs, "Intercellular adhesion, signalling and the cytoskeleton", Nature Cell Biology, 4:E101-E108 (Apr. 2002).
K. Yamanaka et al, "Skin-specific Caspase-1 Transgenic Mice Show Cutaneous Apoptosis and Pre-Endotoxin Shock Condition with a High Serum Level of IL-18.", The Journal of Immunology, pp. 997-1003 (2000).
H. Konishi et al, "IL-18 contributes to the spontaneous development of atopic dermatitis-like inflammatory skin lesion independently of IgE/stat6 under specific pathogen-free conditions.", PNAS, vol. 99 No. 17, pp. 11340-11345, Aug. 20, 2002).
Yong Gu et al, "Activation of Interferon-γ Inducing Factor Mediated by Interleukin-1β Converting Enzyme", Science, 275:206-209 (1997).
H. Tsutsui et al, "Caspase-1-Independent, Fas/Fas Ligand-Mediated IL-18 Secretion from Macrophages Causes Acute Liver Injury in Mice", Immunity 11:359-367 (1999).
E. Seki et al, "Lipopolysaccharide-Induced IL-18 Secretion from Murine Kupffer Cells Independently of Myeloid Differentiation Factor 88 That Is Critically Involved in Induction of Production of IL-12 and IL-1β¹", The Journal of Immunology, pp. 2651-2657 (2001).
Charles A. Dinarello, "Interleukin-1β, Interleukin-18, and the Interleukin-1β Converting Enzyme", Annals New York Academy of Sciences, pp. 1-11 (1998).
G. Fantuzzi and C. A.Dinarello, "Interleukin-18 and Interleukin-1β: Two Cytokine Substrates for ICE (Caspase-1)", Journal of Clinical Immunology, 19(1):1-11 (1999).
H. Okamura et al, "Cloning of a new cytokine that induces INF-γ production by T cells.", Nature,378(6552):88-91 (1995).
T. Yoshimoto et al, "IL-18, although antiallergic when administered with IL-12, stimulates IL-4 and histamine release by basophils", PNAS, 96(24):13962-13966 (1999).
T. Yoshimoto et al, "IL-18 induction of IgE: Dependence on CD4⁺ T cells, IL-4 and STAT6" (Nature Immunology, vol. 1 No. 2, pp. 132-137 Aug. 2000).
T. Hoshino et al, "In vivo administration of IL-18 can induce IgE production though $T_h2$ cytokine induction and up-regulation of CD40 ligand (CD154) expression on CD4⁺ T cells", Eur. J. Immunol, pp. 1998-2006 (2000).
K. Nakanishi et al, "Interleukin-18 Regulates Both TH1 and TH2 Responses", Annu.Rev. Immunol, pp. 423-474 (2001).
K. Thestrup-Pedersen, "Clinical aspects of atopic dermatitis", Clinical and Experimental Dermatology, 25:535-543 (2000).
A. Wollenberg et al, "Atopic dermatitis: pathogenetic mechanisms", Clinical and Experimental Dermatology, 25:530-534 (2000).
T. Tanaka et al, "Interleukin-18 is Elevated in the Sera from Patients with Atopic Dermatitis and from Atopic Dermatitis Model Mice, NC/Nga", Int Arch Allergy Immunol, pp. 236-240 (2001).
T. Yoshimoto et al, "Nonredundant Roles for CD1d-restricted Natural Killer T Cells and Conventional CD4⁺ T Cells in the Induction of Immunoglobulin E Antibodies in Response to Interleukin 18 Treatment of Mice", The Journal of Experimental Medicine, 197(8):997-1005 (2003).
H. Fei et al., "*Staphylococcus aureus* infection and atopic dermatitis", Journal of Clinical Dermatology, 31(6), pp. 402-404 (2002).
B.W. Barry et al., "Mode of Action of Penetration Enhancers in Human Skin", Journal of Controlled Release, vol. 6, pp. 85-97 (1987).

(Continued)

*Primary Examiner* — Rebecca Prouty
*Assistant Examiner* — Paul Martin
(74) *Attorney, Agent, or Firm* — Edwards Wildman Palmer LLP; David G. Conlin; Lisa Swiszcz

(57) ABSTRACT

The present invention provides methods which use induction phenomenon of production of interleukin 18 (IL-18) from keratinocyte (KC), and their usages. The methods are preferably applicable for understanding of pathogenic mechanisms of atopic dermatitis (AD) and AD-like symptoms, and for development of therapeutic drugs for AD and AD-like symptoms. For example, by applying, on skin of mice or the like, protein A (SpA) derived from *Staphylococcus aureus*, or transplanting, on mice, a skin graft which has developed an inflammatory skin disease like AD, it is possible to reproduce elevation of IgE to high level in serum, which elevation is generated in an AD-like lesion. As a result, it is possible, for example, to screen for an inhibitor which inhibits induction of production of IL-18 from KC.

6 Claims, 9 Drawing Sheets

OTHER PUBLICATIONS

V.H.L. Lee et al., "Mucosal Penetration Enhancers for Facilitation of Peptide and Protein Drug Absorption", Ctrical Reviews in Therapeutic Drug Carrier Systems, 8(2), pp. 91-192 (1991).

F. Steindl et al., "A simple method to quantify staphylococcal protein A in the presence of human or animal IgG in various samples", Journal of Immunological Methods, vol. 235, pp. 61-69 (2000).

Abeck et al., "Staphylococcus aureus colonization in atopic dermatitis and its therapeutic implications", British Journal of Dermatology, 139:13-16 (1998).

Ezepchuk et al., "Staphylococcal toxins and Protein A Differentially Induce Cytotoxicity and Release of Tumor Necrosis Factor-α From Human Keratinocytes", The Journal of Investigative Dermatol, 107(4):603-609 (1996).

Kang et al., "Enhanced IL-18 Production by UVB Irradiation Required ROI and AP-1 Signalling in Human Kerationcyte Cell Line HACAT", FASEB Journal (Federation of American Societies for Experimental Biology), 16(4):A670 (2002)—XP009010545 Abstract.

Kato et al., "Monocyte Activation by Staphylococcal Protein A via IgE," Japanese Journal of Dermatology (2001), 111(3):442 (partial English translation included).

Kong et al., "Upregulation of interleukin-18 expression in mouse primary keratinocytes induced to differentiate by calcium", Archives of Dermatological Research, 294(8):370-376 (2002)—XP002378291 Abstract.

Leung et al., "The role of superantigens in human deseases: therapeutic implications for the treatment of skin diseases", British Journal of Dermatology, 139:17-29 (1998).

Leung et al., "Atopic dermatitis," The Lancet (2003) 361:151-160.

Masuda et al., "Biological Property of Staphylococcus aureus and Methodology for Strain Identification," Osaka Regional Meeting of the JDA, Skin vol. 40, Supplement 20, Dec. 1998, pp. 26-31 (partial English translation included).

Naik et al., "Human keratinocytes constitutively express interleukin-18 after treatment with pro-inflammatory mediators and dinitrochlorobenzene", Journal of Investigative Dermatology, 113(5):766-772 (1999)—XP002378294 Abstract.

Nakano et al., "Persistent secretion of IL-18 in the skin contributes to IgE response in mice", International Immunology, 15(5):611-621 (2003).

Sainte-Laudy et al., "Reactivity of human basophils to anti-IgE and protein A in atopic dermatitis," Agents and Actions (1990) 30(1/2):250-253.

Takanami-Ohnishi et al., "Essential role of P38 mitogen-activated protein kinase in contact hypersensitivity", Journal of Biological Chemistry, 277(40):37896-37903 (2002)—XP00238292 Abstract.

Travers et al., "The Keratinocyte as a Target for Staphylococcal Bacterial Toxins", Staphylococcal Toxins and Keratinocytes, 6(3):225-229 (2001).

Tsutsui et al., "Excessive IL-18 of Local Skin Induces Atopic Dermatitis," Journal of Clinical and Experimental Medicine (Igaku no Ayumi) (2003), 205(1):86-91 (partial English translation included).

Unno et al, "Induction of atopic dermatitis-like skin lesion in NC/Nga mice—Influence of the skin barrier destroying solution to the induction of dermatitis-", Areugi, vol. 50(12), pp. 1152-1162 (Dec. 31, 2001) (partial English translation included).

Wehner et al., "Staphylococcus aureus enterotoxins induce histamine and leukotriene release in patients with atopic eczema," British Journal of Dermatology (2001) 145:302-305.

White et al., "Skin response to protein A", Proceedings of the Royal Society of Edinburgh, 79B:43-46 (1980).

Japanese Office Action dated Jan. 6, 2009 for JP2005-506315 (National Phase of PCT/JP2004/005747) (English translation included).

Office Action dated Mar. 31, 2009 issued in related Japanese Application JP 2005-506315 (translation included).

Proksch et al., Integrity of the Permeability Barrier Regulates Epidermal Langerhans Cell Density; . British Journal of Dermatology; vol. 134 (1996) pp. 630-638.

Tsai et al., Tape Stripping and Sodium Dodecyl Sulfate Treatment Increase the Molecular Weight Cutoff of Polyethylene Glycol Penetration Across Murine Skin; Archives of Dermatological Research, vol. 295 (2003) pp. 169-174.

Hiroshi Konishi et al., "IL-18 contributes 1-8, 16 to the spontaneous development of atopic dermatitis-like inflammatory skin lesion independently of IgE/stat6 under specific pathogen-free conditions", Proceeding of the National Academy of Sciences of the United States of America, 99(17), pp. 11340-11345 (2002)—XP 002378293 Abstract.

Nakanishi et al., "Interleukin-18 regulates both TH1 and Th2 responses", Annual Review of Immunology, 19, pp. 423-474 (2001)—XP002378295 Abstract.

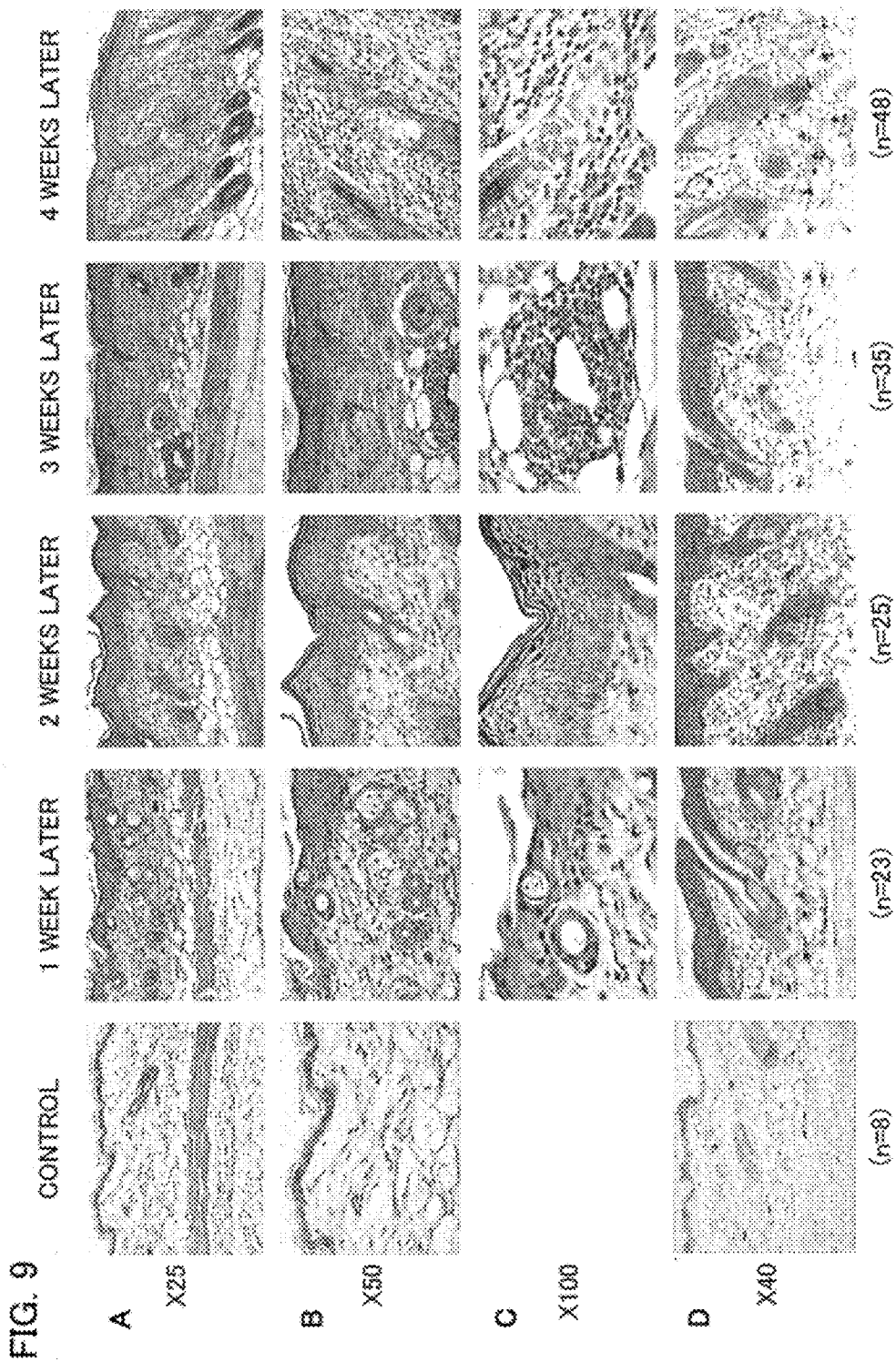

INHIBITOR SCREENING METHOD AND ATOPIC DERMATITIS LIKE SYMPTOM INDUCING METHOD WHICH UTILIZES INDUCTION OF PRODUCTION OF INTERLEUKIN 18 BY KERATINOCYTE AND UTILIZATION OF SAME

CROSS-REFERENCE TO RELATED APPLICATIONS

This application is a divisional of U.S. application Ser. No. 10/554,301 filed Dec. 6, 2006, abandoned, which is a national phase application pursuant to 35 U.S.C. §371 of International Application No. PCT/JP04/05747 filed Apr. 21, 2004, which claims the benefit of priority of Japanese Patent Application No. 2003-120630 filed Apr. 24, 2003. These applications are hereby incorporated herein by reference in their entireties.

TECHNICAL FIELD

The present invention relates to: inhibitor screening method and atopic dermatitis-like symptom inducing method which utilizes induction of production of interleukin 18 by keratinocyte, and utilization of same. Particularly, the present invention relates to: a screening method and an atopic dermatitis-like symptom inducing method preferably applicable to analysis of pathogenic mechanisms of atopic dermatitis and atopic dermatitis-like symptoms, and to development of therapeutic drugs thereof; and usages of the methods.

BACKGROUND ART

Skin is the largest organ in a body, and a forefront for defending a living organism. Epidermis consists of keratinocytes (KC), melanocytes, epidermis Langerhans cells (LC), intraepithelial T cells, and the like.

LC are immature dendritic cells (DC), whose function is to capture and transport locally exposed protein antigen to draining lymph nodes in which acquired immune responses are generally accomplished. During their migration to a lymph node, LC develop into mature DC having antigen-presenting capacity. As a result, a systemic immune response specific to the antigen carried by the LC/DC is caused. In this way, the antigen-specific immune response in the skin is closely associated with the systemic immune response to the same antigen. Therefore, it is thought that skin and immune organs are tightly connected with each other via circulatory trooping of LC/DC and via antigen specific immune cells. On the other hand, KC and melanocytes reside in the skin, and do not principally participate in an acquired immune response.

However, KC might contribute to development of local innate immune response and local inflammation. When microbes infect skin, a host develops an inflammation reaction, and then develops an acquired immune reaction in a manner localized in the skin. At that time, KC and LC constituting the skin are closely involved in each reaction. Therefore, it is thought that, based on their unique property of producing various cytokines upon stimulation from microbes or chemical reagents, KC has a large influence on LC, with a result that KC modify an acquired immune response (see Non-Patent Documents 1 and 2). In consideration of these facts, it is important to determine whether KC-induced cutaneous inflammation can also affect the systemic immune response.

The inventor of the present invention have established caspase-1 transgenic mice (KCASP1Tg mice) which KC-specifically express caspase-1, and develop atopic dermatitis (AD)-like inflammatory skin lesions (pruritic chronic inflammation) in an interleukin 18 (IL-18)- and interleukin 1β (IL-1β)-dependent manner (see Non-Patent Documents 3 and 4). Further, the inventor of the present invention has disclosed that IL-1β enhances the capacity of IL-18 to induce AD-like inflammatory skin lesions (see Non-Patent Document 4). These results suggest that KC may also contribute to the systemic immune response by producing a number of cytokines including IL-18 and IL-1β.

The IL-18 and IL-1β are produced as biologically inert precursors, and are released as an active form after being cleaved by appropriate intracellular enzymes such as caspase-1 (see Non-Patent Documents 5 through 9).

The IL-18 has diverse biological actions depending on the kinds of cytokines coexisting with the IL-18. Particularly, in the presence of interleukin 12 (IL-12), IL-18 promotes inflammatory responses via induction of IFN-γ which is a potent pro-inflammatory cytokine (see Non-Patent Document 10). On the other hand, in the absence of IL-12, IL-18 induces atopic response via induction of production of Th2 cytokine (see Non-Patent Document 11 through 14).

The AD is an inflammatory skin lesion in response to external stimulation, and is accompanied by chronic and repetitive strong itch. The onset of the AD has a genetic basis, and a patient of the AD has high serum levels of IgE. However, the pathogenic mechanism of the AD is poorly understood. Activated T cells, basophil, and mast cells are closely involved in the pathogenic mechanism of the AD.

Particularly, it is thought that as a result of activation of mast cells or basophil by an allergen, Th2 cytokines and chemical mediators are produced, and accordingly AD is developed. The activation of mast cells or basophil by allergen is caused by crosslinking of IgE molecule bound to Fc ε R (Fc receptor (FcR) to IgE antibody of basophil) on these cells. Important ones out of the Th 2 cytokines are, for example, interleukin 4 (IL-4), interleukin 5 (IL-5), interleukin 9 (IL-9), and interleukin 13 (IL-13). Important ones out of the chemical mediators are, for example, histamine, serotonin, and leukotriene.

It is known that infection of *Staphylococcus aureus* exacerbates inflammation of skin of an AD patient according to environments (see Non-Patent Documents 15 and 16), and increases density of serum IL-18 of some AD patients (see Non-Patent Document 17). Namely, it is known that the infection of *Staphylococcus aureus* is an inducing factor or exacerbation factor of AD. However, it is poorly known how *Staphylococcus aureus* is involved in the onset of AD.

[Non-Patent Document 1]

Jamora, C. and Fuchs, E. 2002. Intercellular adhesion, signaling and the cytoskeleton. Nat. Cell Biol. 4:E101

[Non-Patent Document 2]

Grone, A. 2002. Keratinocyte and cytokine. Vet. Immunol. Immunopathol. 88:1.

[Non-Patent Document 3]

Yamanaka, K., Tanaka, M., Tsutsui, H., Kupper, T. S., Asahi, K., Okamura, H., Nakanishi, K., Suzuki, M., Kayagaki, N., Black, R. A., et al. 2000. Skin-specific caspase-1 transgenic mice show cutaneous apoptosis and pre-endotoxin shock condition with a high serum level of IL-18. J. Immunol. 165:997.

[Non-Patent Document 4]

Konishi, H., Tsutsui, H., Murakami, T., Yumikura-Futatsugi, S., Yamanaka, K., Tanaka, M., Iwakura, Y., Suzuki, N., Takeda, K., Akira, S., Nakanishi, K., and Mizutani, H. 2002. IL-18 contributes to the spontaneous development of an atopic dermatitis-like inflammatory skin lesion independently of IgE/stat6 under specific pathogen-free conditions. Proc. Natl. Acad. Sci. USA. 99:11340.
[Non-Patent Document 5]
Gu, Y., Kuida, K., Tsutsui, H., Ku, G., Hsiao, K., Fleming, M. A., Hayashi, N., Higashino, K., Okamura, H., Nakanishi, K., et al. 1997. Activation of interferon-γ inducing factor mediate by interleukin-1β converting enzyme. Science 275: 206.
[Non-Patent Document 6]
Tsutsui, H., Kayagaki, N., Kuida, K., Nakano, H., Hayashi, N., Takeda, K., Matsui. K., Kashiwamura, S., Hada, T., Akira, S., et al. 1999. Caspase-1-independent, Fas/Fas ligand-mediated IL-18 secretion from macrophages causes acute liver injury in mice. Immunity 11:359.
[Non-Patent Document 7]
Seki, E., Tsutsui, H., Nakano, H., Tsuji, N. M., Hoshino, K., Adachi, O., Adachi, K., Futatsugi, S., Kuida, K., Takeuchi, O., et al. 2001. LPS-induced IL-18 secretion from murine Kupffer cells independently of IL-12 and IL-1β. J. Immunol. 169:3863.
[Non-Patent Document 8]
Dinarello, C. A. 1998. Interleukin-1β, interleukin-18, and the interleukin-1β converting enzyme. Ann. NY Acad. Sci. 856:1
[Non-Patent Document 9]
Fantuzzi, G. and Dinarello, C. A. 1999. Interleukin-18 and interleukin-1β: two cytokine substrates for ICE (caspase-1). J. Clin. Immunol. 19:1.
[Non-Patent Document 10]
Okamura, H., Tsutsui, H., Komatsu, T., Yutsudo, M., Hakura, A., Tanimoto, T., Torigoe, K., Okura, T., Nukada, Y., Hattori, K., Akita, H., Namba, M., Tanabe, F., Konishi, K., Fukada, S., and Kurimoto, M. 1995 Cloning of a new cytokine that induces INF-γ production by T cells. Nature 378:88.
[Non-Patent Document 11]
Yoshimoto, T., Tsutsui, H., Tominaga, K., Hoshino, K., Okamura, H, Akira, S., Paul, W. E. and Nakanishi, K. 1999. IL-18, although anti-allergic when administered with IL-12, stimulates IL-4 and histamine release by basophils. Proc. Natl. Acad. Sci. USA 96:13962.
[Non-Patent Document 12]
Yoshimoto, T., Mizutani, H., Tsutsui, H., Noben-Trauth, N., Yamanaka, K., Tanaka, M., Izumi, S., Okamura, H., Paul, W. E. and Nakanishi, K. 2000. IL-18 induction of IgE: Dependence on CD4$^+$ T cells, IL-4 and STAT6. Nat. Immunol. 1:132.
[Non-Patent Document 13]
Hoshino, T., Yagita, H., Wiltrout, R. H. and Young, H. A. 2000. In vivo administration of IL-18 can induce IgE production through Th2 cytokine induction and up-regulation of CD40 ligand (CD154) expression on CD4$^+$ T cells. Eur. J. Immunol. 30:1998.
[Non-Patent Document 14]
Nakanishi, K., Yoshimoto, T., Tsutsui, H. and Okamura, H., 2001. Interleukin-18 regulates both Th1 and Th2 responses. Annu. Rev. Immunol. 19:423.
[Non-Patent Document 15]
Thestrup-Pedersen, K. 2000. Clinical aspects of atopic dermatitis. Clin. Exp. Dermatol. 25:535.
[Non-Patent Document 16]
Wollenberg, A., Kraft, S., Oppel, T. and Bieber, T. 2000. Atopic dermatitis: pathogenetic mechanisms. Clin. Exp. Dematol. 25:530.
[Non-Patent Document 17]
Tanaka, T., Tsutsui, H., Yoshimoto, T., Kotani, M., Masumoto, M., Fujita, A., Wang, W., Higa, S., Kishimoto, T., Nakanishi, K., et al. 2001. Interleukin-18 is elevated in the sera from patients with atopic dermatitis and from atopic dermatitis model mice, NC/Nga. Int. Arch. Allergy Immunol. 125:236.

At present, the pathogenic mechanism of AD is poorly understood, and therefore it is very difficult to develop an effective therapeutic drug for AD.

As described above, it is known that cells constituting epidermis are involved in a variety of immune responses. For example, it is recently reported that dendritic cells induce an acquired immune response as antigen presenting cells. However, as for KC which are the most main cells out of cells constituting epidermis, it is not clear how KC are involved in immune response of a host.

In developing an effective therapeutic drug for a given disease, it is one of important methods to understand the pathogenic mechanism of the disease, and to perform, by use of the mechanism, screening of a substance having a pharmacological effect. However, as for the onset of AD, there are a lot of unsolved points including involvement of KC and infection of *Staphylococcus aureus*. Therefore, a technique (including screening) for applying them to the development of a therapeutic drug for AD is rarely known.

The present invention is made in view of the foregoing problems, and its object is to provide, by means of an induction phenomenon of generation of IL-18 from KC, a variety of methods preferably applicable to solution of the pathogenic mechanisms of atopic dermatitis and atopic dermatitis-like symptoms, and for development of a therapeutic drug for atopic dermatitis and atopic dermatitis-like symptoms, and usages of the methods.

DISCLOSURE OF INVENTION

The inventor of the present invention has studied the foregoing problems, and verified in vitro and in vivo that protein A derived from *Staphylococcus aureus* stimulates KC and induces generation of IL-18. As a result, the present invention has been completed.

The method according to the present invention for screening for an inhibitor uses induction of production of interleukin 18 in a living organism having an inflammatory skin lesion like atopic dermatitis, and includes: an environment conditioning step for conditioning, in vivo or in vitro, an environment in which the production of interleukin 18 from keratinocyte is induced by stimulation with a stimulator; and an inhibitor identifying step for administering a candidate-substance under the environment and identifying, as the inhibitor, a substance which inhibits the induction of the production of interleukin 18 from the keratinocyte.

In the method, it is preferable that the stimulator is at least one of (i) protein A derived from *Staphylococcus aureus*, (ii) partial protein of the protein A, the partial protein being capable of stimulating keratinocyte, and (iii) a mutant of the protein A or of partial protein of the protein A, the mutant being capable of stimulating keratinocyte. Further, it is preferable that, as the stimulator, Sodium dodecyl sulfate (SDS) as well as protein A is used.

Further, in the method, it may be that, in the environment conditioning step carried out in vitro, the environment is realized by incubating culture cells of keratinocyte with a culture solution to which the protein A is added. It may be that, in the environment conditioning step carried out in vivo, the environment is realized by applying the protein A on skin of the living organism provided as a host.

Further, it may be that, in the environment conditioning step carried out in vivo, the environment is realized by using, as the stimulator, a skin graft on which an inflammatory skin lesion like atopic dermatitis is developed, and transplanting the skin graft on the living organism provided as a host.

Here, it is preferable that the living organism provided as the host is at least such that CD4+ T cells normally exist, that stat6 is expressed, and that NKT cells constitutively express IL-18Rα chain. For example, the living organism provided as the host is a mouse.

Further, the present invention includes a therapeutic drug for an immune disease, including an inhibitor obtained by using the method of screening. Further, the present invention includes a method for inhibiting high-level IgE in serum in a living organism having an inflammatory skin lesion like atopic dermatitis, the method using an inhibitor obtained by using the method as set forth in any one of claims 1 through 8, or the therapeutic drug as set forth in claim 9, so as to inhibit systemic IgE response caused, without exposure to an antigen, by local accumulation of interleukin 18 from keratinocyte.

The method according to the present invention for inducing atopic dermatitis-like symptom causes a model organism to develop an inflammatory skin lesion like atopic dermatitis, and includes the step of applying, on skin of the model organism, protein A derived from *Staphylococcus aureus*.

In the method of induction, the protein A is at least one of (i) complete protein of the protein A, (ii) partial protein of the protein A, the partial protein being capable of stimulating keratinocyte, and (iii) a mutant of the protein A or of partial protein of the protein A, the mutant being capable of stimulating keratinocyte. Further, it is preferable that when the protein A is applied on skin of a model organism, SDS is used as well as the protein A.

Further, the present invention includes a model organism which develops an inflammatory skin lesion obtained by means of the method of induction, and an example of the model organism is a mouse.

The usage of the present invention is, for example, a screening kit for carrying out the method of screening, or an inducing kit for carrying out the method of induction.

Each of the methods uses the fact that in an inflammatory skin lesion like atopic dermatitis (AD), local accumulation of IL-18 produced from keratinocyte causes, without exposure to an antigen, a systemic IgE response. As such, each of the methods is preferably applicable for understanding of atopic dermatitis and atopic dermatitis-like symptoms, and for development of therapeutic drugs for atopic dermatitis and atopic dermatitis-like symptoms.

Additional objects, features, and strengths of the present invention will be made clear by the description below. Further, the advantages of the present invention will be evident from the following explanation in reference to the drawings.

BRIEF DESCRIPTION OF DRAWINGS

FIGS. 9A through 9D are views illustrating the results of observation by a microscope of a change with times in skin of NC/Nga mice on which mixture of 4% SDS and SpA (200 µg/day) is applied, as well as the results of controls.

BEST MODE FOR CARRYING OUT THE INVENTION

Figure 1:
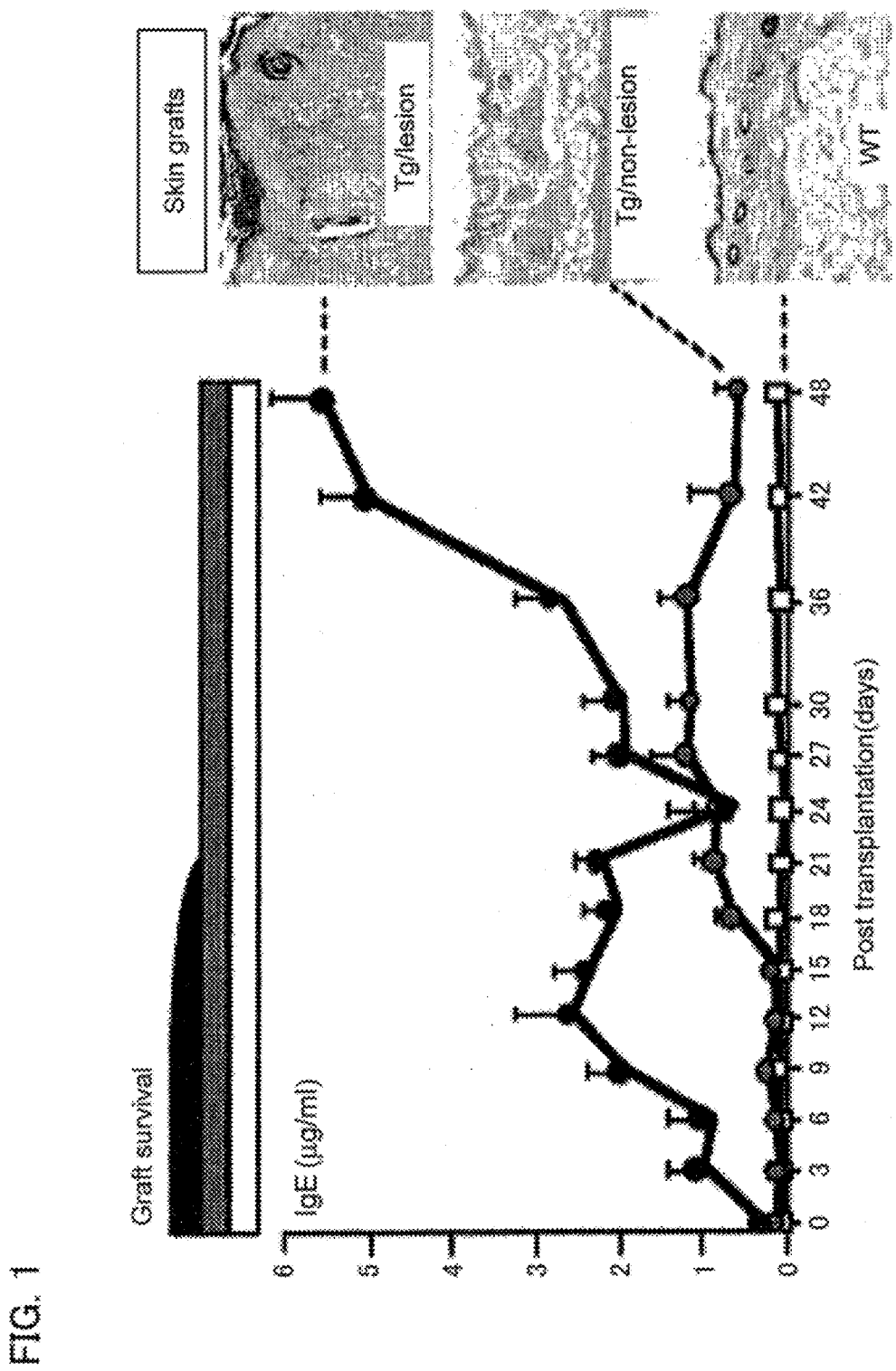
FIG. 1 is a view illustrating the result of IgE induction in a host, caused by transplanting lesion skin of KCASP1Tg mice, as well as the result of a control.

The inventors of the present invention found out that local accumulation of IL-18 produced from keratinocyte causes, without exposure to an antigen, a systemic IgE response, which brings about an inflammatory skin lesion like atopic dermatitis. In the present invention, using the finding, a screening method preferably applicable for understanding of the pathogenic mechanisms of atopic dermatitis and atopic dermatitis-like symptoms, and for development of therapeutic drugs therefor, and a method for inducing atopic dermatitis-like symptoms, and usages of the methods, are realized. The present invention is specifically explained below.

(1) Screening Method According to Present Invention

The screening method according to the present invention includes an environment conditioning step of forming an environment in which local production of IL-18 from keratinocyte (KC) is induced by stimulation with a stimulator, and an inhibitor identification step of administering a candidate-substance under the environment, and for identifying, as the inhibitor, a substance which inhibits induction of the production of interleukin 18 from KC.

In an inflammatory skin lesion like atopic dermatitis, IL-18 is excessively produced from some regions of KC of skin, and thereby high-level IgE sometimes occurs in serum. Therefore, use of a screening method including the environment conditioning step and the inhibitor identification step makes it possible to obtain a substance which inhibits secretion of IL-18. The obtained substance (inhibitor) can be an effective therapeutic drug for AD.

The term "the inflammatory skin lesion like AD" in the present invention encompasses any immune diseases which develop dependently on IL-18 and whose symptom is inflammation on skin, and is not limited to pruritic chronic inflammation which is strictly discerned as AD.

Further, what is meant by the term "in vitro" in the present invention is a reaction system artificially reproduced by using culture cells, and what is meant by the term "in vivo" is a reaction system absolutely in an individual.

Further, "inhibitor" of the present invention may be any substance that inhibits the secretion of IL-18 from KC, and the present invention is not particularly limited in terms of inhibiting mechanism. Therefore, an inhibitor obtained by the screening method according to the present invention may be a one which reversibly inhibits a process of secretion of IL-18 from the KC, or a one which irreversibly inhibits the process. Further, when the inhibitor is a one which reversibly inhibits the process, the inhibitor may be an inhibitor (antagonist) in a competitive (antagonistic) type, or an inhibitor in a non-antagonistic type. In other words, the screening method according to the present invention can screen a wide variety of inhibitors including antagonists.

[Environment Conditioning Step]

The environment conditioning step may be any step as long as the step can condition an environment in which local production of IL-18 from keratinocyte (KC) is induced by stimulation with a stimulator, and how to condition the environment is not particularly limited. Namely, the environment conditioning step may be in vivo or in vitro as long as the step can realize an environment in which generation of IL-18 can be induced.

Examples of the stimulator are a variety of protein (KC stimulating protein) capable of stimulating KC. The KC stimulating protein is not particularly limited as long as it can stimulate KC. A typical example of the KC stimulating protein is protein A (SpA) produced from *Staphylococcus aureus*.

As described above, it has been known so far that infection with *Staphylococcus aureus* is an inducing factor or exacerbation factor of AD. Further, the inventors of the present invention found that, when SpA, together with SDS is applied to a mouse, pruritic chronic inflammation like AD can be induced in a short time (see the examples). Therefore, the SpA can be preferably used as KC stimulating protein.

The SpA may be complete protein (protein having a complete amino acid sequence) derived from *Staphylococcus aureus*. However, as long as the SpA can stimulate keratinocyte, the SpA may be partial protein of SpA, or engineered protein of the complete protein or the partial protein.

What is meant by the term "engineered protein" is protein which has an amino acid sequence of known SpA, with one or several amino acids replaced, deleted, inserted, and/or added, and which negatively controls expression of B7-2 molecule on a surface of cells. Further, what is meant by the wording "one or several amino acids are replaced, deleted, inserted, and/or added" is to replace, delete, insert, and/or add amino acids (preferably, no more than 10 amino acids, more preferably, no more than 7 amino acids, and further preferably, no more than 5 amino acids) in number which can be replaced, deleted, inserted, and/or added by a known method of producing mutated protein, such as site-specific mutagenesis. In this way, the engineered protein is mutant protein of the SpA, and what is meant by the term "mutation" here is mutation artificially induced by a known method of producing mutant protein. However, the engineered protein may be produced by isolating and refining similar mutant protein existing in nature. Further, the engineered protein of the SpA may include additional polypeptide.

Further, it is preferable to use, as the stimulator, SDS together with SpA. When SDS and protein A are used together, it is possible to induce more severe pruritic chronic inflammation like AD (see Examples). How to use SpA and SDS in combination is not particularly limited, but it is preferable to prepare a SpA-SDS solution made by adding SDS to a medium in which SpA is dissolved, and to apply the solution on the skin of a model organism.

[Method of Stimulating KC]

The method of stimulating KC with the KC stimulating protein is not particularly limited, and it may be any method as long as it can stimulate KC so as to induce the production of IL-18. To be specific, for example, in the case of the in vitro environment conditioning step, culture cells of KC are cultured with a culture solution to which SpA is added. The culture cells of KC used here are not particularly limited, and known culture cells can be preferably used. For example, in a later-mentioned example 6, PAM212 cells were used.

Culture conditions of the culture cells of the KC, such as a culture solution, culture temperature, and a method for adding SpA are not particularly limited, and suitable conditions may be set according to the kinds of culture cells to use.

On the other hand, in case of the in vivo environment conditioning step, SpA is applied on skin of an individual to be a host. Conditions under which SpA is applied is not particularly limited, and the method for applying may be any one as long as it does not prevent stimulation of KC with SpA. For example, in later Examples, SpA is used as a PBS solution of 50% glycerol, but the present invention is not limited to this. Further, as described above, the SpA-SDS solution prepared by adding SDS to SpA may be applied on the skin of the host. Conditions of applying of SpA such as a method for applying and to which portion of the host SpA is to be applied are not particularly limited.

The host used here is not particularly limited. Typically, mammals generally used in a variety of experiments may be used. To be specific, laboratory animals such as mice, rats, rabbits, pigs, and monkeys may be used as the host. For example, in a later-mentioned example, mice are used as the host. Mice are particularly preferable because of such advantages that they are widely used as laboratory animals, that a variety of breeds of mutants are easily obtained, and that small bodies of mice allow a space for breeding to be comparatively small.

[Skin Specimen Transplantation]

In the case of the in vivo environment conditioning step, a substance other than KC stimulating protein such as SpA can be used as the stimulator. A typical example is skin (lesion skin) on which an inflammatory skin lesion like AD is generated. The transplantation of a lesion skin specimen on the host makes it possible to realize an environment in which the production of IL-18 is induced.

The lesion skin is not particularly limited as long as it is skin on which an inflammatory skin lesion like AD is generated. However, due to implantation, it is very preferable that the skin be that of an organism of the same species as the host. Using skin of an organism of a species different from the host is not preferable because the transplantation of such skin causes immune response due to other than the inflammatory skin lesion, such as rejection. As described in the explanation about the KC stimulating protein, the host may be a variety of laboratory animals. When mice are used as a host, it is very preferable that a lesion skin specimen to be transplanted is mice-derived (see later-mentioned Examples).

Here, it is necessary that the host have characters such as (i) expression of $CD4^+$ T cells, (ii) expression of stat6, and (iii) expression of IL-18Rα chain. As is obvious from the result of later-mentioned Example 4, when a lesion skin specimen obtained from KCASP1Tg mice was transplanted to CD4-deficient mice, stat6-deficient mice, IL-18Rα chain-deficient mice, the production of IgE was not induced in neither mice. Namely, in order to realize the environment in which the production of IL-18 is induced, the characters such as (i), (ii), and (iii) are necessary.

The $CD4^+$ T cells are T cells that express antigen CD4 (one of cell membrane glycoprotein of helper cells). The reference "+" or "−" located at upper right indicates whether or not the cells express CD4. Therefore, the cells that express CD4 are indicated by "$CD4^+$" and the cell that do not express CD4 are indicated by "$CD4^-$." Further, the stat6 (STAT6) is an intracellular signal transmission molecule which is involved in an action mechanism of cytokine, and which is activated specifically by IL-4. The IL-18Rα chain is expressed on T cells and is involved in response of IL-18.

[Inhibitor Identification Step]

The inhibitor identification step is not particularly limited, as long as the step administers candidate-substances under the environment which is conditioned in the environment conditioning step and in which generation of IL-18 is induced, and identifies a substance which inhibits the induction of the production of interleukin 18 by keratinocyte. The substance identified by the step can be an inhibitor for inhibiting the induction of the secretion of IL-18.

The method for administering the candidate-substance is not particularly limited. For example, in vitro, it may be that the candidate-substance is administered to a culture solution for incubation of culture cells of KC. In vivo, it may be that the candidate-substance is applied on an inflammatory portion of the host, or that the host is orally administered with the candidate-substance. Further, the method for identifying the inhibitor is not particularly limited as long as the method can surely confirm that the induction of the production of IL-18 by KC is inhibited. Both in the in vitro and in vivo environments in which the production of IL-18 is induced, it is possible to use cell-free system and the like using ELISA.

The present invention is not particularly limited in terms of the screening method as long as the screening method includes the environment conditioning step and the inhibitor identification step. Of course, the screening method may include other step or steps.

[Therapeutic Drug for Immune Disease and Method for Inhibiting High-Level IgE]

Further, the present invention includes a therapeutic drug for an immune disease. The therapeutic drug contains an inhibitor obtained through the screening method. Concrete composition and the like of the therapeutic drug are not particularly limited, as long as the therapeutic drug contains a suitable buffer or additive according to the kind of the screened inhibitor, and to a state of an individual (including human being) to which the therapeutic drug is to be administered.

Further, the present invention includes a method for inhibiting high-level IgE by using the inhibitor obtained through the screening method, or by using the therapeutic drug. Using the inhibitor or the therapeutic drug, the method inhibits systemic IgE response that is caused, without exposure to an antigen, by local accumulation of IL-18 produced from KC. As a result, it is possible to inhibit high-level IgE in serum caused when an inflammatory skin lesion like atopic dermatitis occurs.

The induction of the production of IL-18 from KC sometimes directly causes AD, and sometimes causes high-level IgE, which leads to AD. In either case, the present invention can effectively treat or mitigate the condition of AD.

(2) Atopic Dermatitis-Like Symptom Inducing Method According to Present Invention In (1), the method for screening a therapeutic drug for AD and AD-like symptom from candidate-substances is explained. However, the present invention is not limited to this, and includes a method for inducing an atopic dermatitis-like symptom, in which a model organism is caused to develop an inflammatory skin lesion like AD, for the purpose of understanding the pathogenic mechanism of AD and AD-like symptom.

The method according to the present invention for inducing the AD-like symptom may be a method for applying, on the host, protein A produced from *Staphylococcus aureus*, as described in the case of using the KC stimulating protein as a stimulator in the environment conditioning step of (1). The applying condition and the like in this method is not particularly limited, as with the applying condition and the like of (1).

Further, as described in (1), the protein A may be at least one of (i) complete protein of the protein A, (ii) partial protein of the protein A, the partial protein being capable of stimulating keratinocyte, and (iii) a mutant of the protein A, or of the partial protein of the protein A, the mutant being capable of stimulating keratinocyte.

Further, as described above, laboratory animals such as mice, rats, rabbits, pigs, and monkeys, particularly mice and the like, can be preferably used as the host. In other words, the present invention includes a model organism which has developed the inflammatory skin lesion due to the induction by the inducing method.

(3) Usage of Present Invention

As described above, the screening method according to the present invention and the method according to the present invention for inducing an AD-like symptom can be preferably used for understanding the pathogenic mechanism of AD and AD-like symptom, and for developing a therapeutic drug therefor. Here, the methods according to the present invention may be realized by a kit. Namely, the present invention may include a screening kit for performing the screening method or an inducing kit for performing the method for inducing the AD-like symptom.

The screening kit may have any arrangement with no particular limitation. For example, the screening kit may be arranged to include at least a stimulator (particularly KC stimulating protein and an accelerator) and a variety of materials (for example, SpA binding protein and a signal transfer molecule) for use in the inhibitor identification step. Similarly, the inducing kit for the AD-like symptom may have any arrangement with no particular limitation. For example, the inducing kit may be arranged to include applying means for effectively applying a SpA solution and SpA.

The screening method according to the present invention is preferably used for screening for a therapeutic drug for an immune disease, which therapeutic drug cures an AD-like inflammatory skin lesion. Further, the method according to the present invention for inducing the AD-like symptom can be used for understanding the pathogenic mechanism of the AD-like symptom, by causing the model organism to artificially develop the AD-like symptom, and further, can be used for verifying the effect of the inhibitor obtained by the screening method according to the present invention.

For example, assume that, using the screening method according to the present invention including the in vitro environment conditioning step, a given inhibitor (for example, substance X) can be obtained. In this case, an effect of the substance X in culture cells of KC is observed. As such, it is possible to produce mice that has developed AD-like symptom by using the method according to the present invention for inducing an AD-like symptom, and to verify the effect of the substance X by using the mice.

The usage of the present invention is not limited to the arrangements exemplified above, and may be applied to a variety of other ways.

As described above, in the present embodiment, the present invention was explained referring to concrete arrangements that exemplify the present embodiment, but the present invention is not limited to the embodiment, and may be carried out with a variety of modifications, changes, correction, based on the knowledge of a person with ordinary skill in the art, within the scope of the invention.

The present invention is further explained in detail below with Examples and Comparative Examples. However, the present invention is not limited to those. Note that mice, reagents, and concrete details of experiment methods used in Examples are explained below.

[Mice]

Female C57BL/6(B6) wild-type mice (6-10 weeks old) were purchased from CLEA Japan. CD4-deficient mice on a B6 background (female, 6-10 weeks old) were kindly provided by Dr. Taniguchi of University of Tokyo. Stat6-deficient mice produced on a B6 background (female, 6-10 weeks old) were kindly provided by of Dr. Takeda of Osaka University (see Takeda, K., Tanaka, T., Shi, W., Matsumoto, M., Minami, M., Kashiwamura, S., Nakanishi, K., Yoshida, N., Kishimoto, T. and Akira. S., 1996. Essential role of STAT6 in IL-4 signaling. Nature 380:627) IL-18Rα-deficient mice obtained by crossbreeding B6 mice and F10 mice (female, 6-10 weeks old) were kindly provided by Dr. Hoshino of Osaka University (see Hoshino, K., Tsutsui, H., Kawai, T., Takeda, K., Nakanishi, K., Takeda, Y. and Akira, S. 1999. Generation of IL-18 receptor-deficient mice: evidence for IL-1 receptor-related protein as an essential IL-18 binding receptor. J. Immunol. 162:5041)

As donors of skin grafts, female mice suffering from chronic dermatitis with high serum levels of IgE (10-12 µg/ml) and IL-18 (5-7 ng/ml) were selectively used. F6 mice (female, 6-10 weeks) obtained by crossbreeding caspase-1-deficient mice and B6 wild-type mice were used (see Seki, E., Tsutsui, H., Tsuji, N. M., Hayashi, N., Adachi, K., Nakano, H., Futatsugi-Yumikura, S., Takeuchi, O., Hoshino, K., Akira, S., Fujimoto, J. and Nakanishi, K. 2002. Critical roles of myeloid differentiation factor 88-dependent proinflammatory cytokine release in early phase clearance of *Listeria monocytogenes* in mice. J. Immunol. 169:3863). Myeloid differentiation factor 88 (MyD 88)-deficient mice on a B6/129 background and F4 mice of Toll-like receptor (TLR) 2-deficient mice were kindly provided by Dr. Akira of Osaka University (See Seki et al). All mice were maintained under specific pathogen-free conditions.

[Reagent]

SpA purified from *Staphylococcus aureus* Cowan 1 was purchased from Calbiochem. Lipopolysaccharide (LPS) obtained from *Escherichia coli* (O55; B5) was purchased from Difco. As for murine Fas ligand transfectant, see Non-Patent Document 6. Z-VAD-FMK (ZVAD), a caspase inhibitor for widely preventing the activity of caspase, and Ac-YCAD-CMK (YVAD), a specific caspase-1 inhibitor, were purchased from Peptide Institute. In the present embodiment, RPMI 1640 containing 10% FCS, 100 U/ml penicillin, 100 µg/ml streptomycin, 50 µM 2-mercaptoetanol and 2 mM L-glutamine was used as a normal culture solution. Keratinocyte cell strain PAM212 of mice was kindly provided by Dr. Tamaki of University of Tokyo.

[Skin Transplantation]

Skin specimens (1 cm$^2$) were prepared from normal skin of wild-type B6 mice or lesion-developing skin (lesion skin) or lesion-undeveloping skin (non-lesion skin) of KCASP1Tg mice, and then were transplanted onto the backs of wild-type B6, CD4-deficient, stat6-deficient, or IL-18Rα-deficient B6 mice. As skin specimens, two pieces of implants of lesion skin or non-lesion skin were prepared.

After skin transplantation, the recipients were fed with drinking water supplemented with 1 mg/ml neomycin sulfate (manufactured by Sigma) and 1000 U/ml polymixin B sulfate (manufactured by Sigma), so as to prevent any possible infection. Serum was suitably sampled so as to determine IgE concentration.

Graft survival of transplanted skin on each host transplanted with the skin was observed up to 48 days. For histological study, skin specimens were stained with hematoxylin and eosin (see Non-Patent Documents 3 and 4).

[Skin Lysate]

Skin specimens (1 cm$^2$) were prepared from wild-type B6 mice or KCASP1Tg mice, and then a sheet of epidermis prepared from the skin specimens were homogenized in PBS (phosphoric acid-buffered physiological saline) at 4° C. and filtered. Concentrations of cytokines and proteins contained in each lysate were detected by ELISA kits using a reagent for cytokine and a protein assay reagent (manufactured by Pierce).

[Th1/Th2 Differentiation]

Splenic CD4$^+$ T cells were isolated from variously treated mice using an AutoMACS™ separator (manufactured by Miltenyi Biotec). The newly isolated spleen cells were incubated with anti-CD4 beads (manufactured by Miltenyi Biotec). The purity of the CD4$^+$ T cells was more than 98%. The cells (1×10$^6$/ml) were incubated with immobilized anti-CD3ε (manufactured by PharMingen) for 48 hours. Concentrations of IFN-γ and IL-4 in each supernatant were determined by ELISA.

[Assay for Cytokines and IgE]

Concentration of IL-18 was determined by an ELISA kit manufactured by MBL. IL-4, IFN-γ, and IL-1β were determined by an ELISA kit manufactured by Genzyme. An ELISA kit for IL-5 was purchased from Endogen. IgE serum level was determined by an ELISA kit manufactured by pharMingen. IFN-γ induction ability of IL-18 was determined by bioassay using clones of IL-18-responsive mouse NK cells (see Non-Patent Document 6 and others)

To be specific, LNK5E6 cells, having higher responsiveness to stimulation with IL-18 in terms of IFN-γ production than LNK5E3 cells (see Non-Patent Document 6), were incubated with a variety of samples and 100 pg/ml IL-12, in the presence or absence of anti-IL-18 antibody (50 µg/ml), for 48 hours. As described in a next equation, activity of IL-18 is defined as concentration of IFN-γ produced by the cells in response to IL-18 (see Non-Patent Document 6)

IL-18 activity=(IFN-γ in supernatant without anti-IL-18 antibody)-(IFN-γ in supernatant with anti-IL-18 antibody).

[Application of SpA]

Solutions made by dissolving various doses of SpA in 5 µl vehicle (50% glycerol in PBS) were prepared, and the SpA solutions were applied on ear skin of wild-type mice for 14 days. For the control study, 5 µl vehicle without SpA was used. One mouse was caged to avoid effects from other mice.

[Preparation of KC]

KC were prepared from various genotypes of mice, according to the method described by Dr. Tamaki et al (see Vestergaard, C., Yoneyama, H., Murai, M., Nakamura, K., Tamaki, K., Terashima, Y., Imai, T., Yoshie, O., Irimura, T., Mizutani, H., et al. 1999. Overproduction of Th2-specific chemokine in NC/Nga mice exhibiting atopic dermatitis-like lesions. J. Clin. Invest. 104:1097, or Tamaki, K., Stingl, G., Gullino, M., Sachs, D. H. and Katz, S. I. 1979. 1a antigens in mouse skin are predominantly expressed on Langerhans cell. J. Immunol. 123:784), and were incubated in a medium overnight, so as to normally recover their surface molecule expression. In order to delete DC, KC were incubated with CD11c microbeads (manufactured by Miltenyi Biotec), and then CD 11c$^+$ cells were depleted using an AutoMACS™ separator.

KC (5×10$^5$/ml) or PAM212 cells (2×10$^5$/ml) were incubated with a variety of doses of SpA and 1 µg/ml LPS or mFasL (1×10$^6$/ml) for 24 hours. In some examples, KC of wild-type mice were incubated with 100 µg/ml SpA in the presence of 20 µM of ZVAD or YVAD for 24 hours. IL-18 concentration and its activity in each supernatant were determined by ELISA and bioassay respectively. In some examples, KC were incubated with 500 μg/ml SpA for 4 hours, and total RNA was extracted, followed by RT-PCR (see Tsutsui, H., Matsui, K., Kawada, N., Hyodo, Y., Hayashi, N., Okamura, H., Higashino, K. and Nakanishi, K. 1997. IL-18 accounts for both TNF-α and Fas ligand-mediated hepatotoxic pathways in endotoxin-induced liver injury in mice. J. Immunol. 159:3961). As to primers for IL-18, IL-12p35, IL-12p40, or β-actin, and PCR conditions for individual cytokines, see the Tsutsui et al.

[Preparation of Kupffer Cells]

Kupffer cells were prepared according to Non-Patent Document 6. Kupffer cells ($1 \times 10^6$/ml) were incubated with 1 μg/ml LPS (lypopolysaccharide) for 4 hours, and their IL-18, IL-12p35, IL-12p40 and β-actin expressions were determined as mRNA levels by RT-PCR.

[FACS (Fluorescence Activated Cell Sorter) Analysis]

Proportions of DC, $CD4^+$ T cells and $CD8^+$ T cells were determined by two-color flow cytometric analysis, after KC having been prepared according to Non-Patent Document 6 were incubated with phycoerythrin (PE)-conjugated anti-CD 11c antibody (manufactured by PharMingen) and fluorescein isothiocyanate (FITC)-conjugated anti-I-Ab antibody (manufactured by PharMingen), or incubated with PE-conjugated anti-CD4 antibody (manufactured by PharMingen) and FITC-conjugated anti-CD8 antibody (manufactured by PharMingen).

[Statistics]

All data were shown as mean and standard deviation of three samples. Significance between a control group and a treated group was examined by an independent Student's test. $P<0.05$ was considered significant.

EXAMPLE 1

Induction of IgE by Transplantation of Skin Graft from KCASP1Tg Mice

First, it was examined whether transplantation of lesion skin of KCASP1Tg mice to syngeneic normal wild-type mice induces elevation of serum levels of IgE. To be specific, in order to normalize the conditions of skin grafts in each transplantation, KCASP1Tg mice that had suffered from chronic dermatitis in their ears, faces and trunks, and had certain levels of IL-18 and IgE in their sera were selected as donors. Grafts of lesion or non-lesion skin of KCASP1Tg mice were transplanted onto normal B6 mice, and serum levels of IgE of hosts were measured. The result of the measurement is illustrated in FIG. 1.

In FIG. 1, closed circles in the graph and the photograph in upper right illustrate the result of transplantation of lesion skin of KCASP1Tg mice to normal B6 mice. Hatched circles in the graph and the photograph in middle right illustrate the result of transplantation of non-lesion skin of KCASP1Tg mice. Open squares in the graph and the photograph in lower right illustrate the result of transplantation of normal skin of wild-type mice. At the time points indicated in the graph, sera were sampled for measurement of IgE by ELISA, and graft survival of transplanted skin was observed (the upper side of FIG. 1: graft survival of transplanted skin). Data items illustrate mean and standard deviation of three mice in each experiment group. The graft survival of transplanted skin is illustrated in the upper panel.

As illustrated in FIG. 1, non-lesion skin-grafted B6 mice showed delayed and poor IgE response, and on the other hand serum levels of IgE of lesion skin-grafted mice increased at an early stage. B6 mice provided as controls, that had been transplanted with skin grafts of wild-type mice, showed no elevation of IgE. Lesion skin-grafted B6 mice showed high IgE levels in their sera, but decreased the levels after detachment of grafts. On the other hand, non-lesion skin-grafted B6 mice maintained low IgE levels. Further, lesion skin-grafted B6 mice started to increase again their serum IgE levels after rejection of lesion skin grafts.

Note that serum levels of IL-18 were not elevated after stimulations of any type of skin grafts (data is not shown). Serum IL-4 or IL-6 was not detected by commercially available ELISA kits (data is not shown). These results indicate that lesion skin of KCASP1Tg mice is capable of inducing long-lasting systemic IgE elevation when transplanted onto normal B6 mice. This is contrary to exogenous IL-18-dependent IgE production that ceased immediately after stopping administration of IL-18 (data is not published).

EXAMPLE 2

Concentration of IL-18-and-Th2-related Cytokine in Lesion Skin of KCASP1Tg Mice

In order to understand the mechanism by which only transplantation of lesion skin can efficiently induce IgE responses in the host, grafts of lesion skin and grafts of non-lesion skin were compared with each other in terms of the concentration of IL-18. The concentration of IL-18 was measured after the grafts of each skin were lysed. The results of the measurements are illustrated in FIGS. 2A through 2F.

Figure 2:
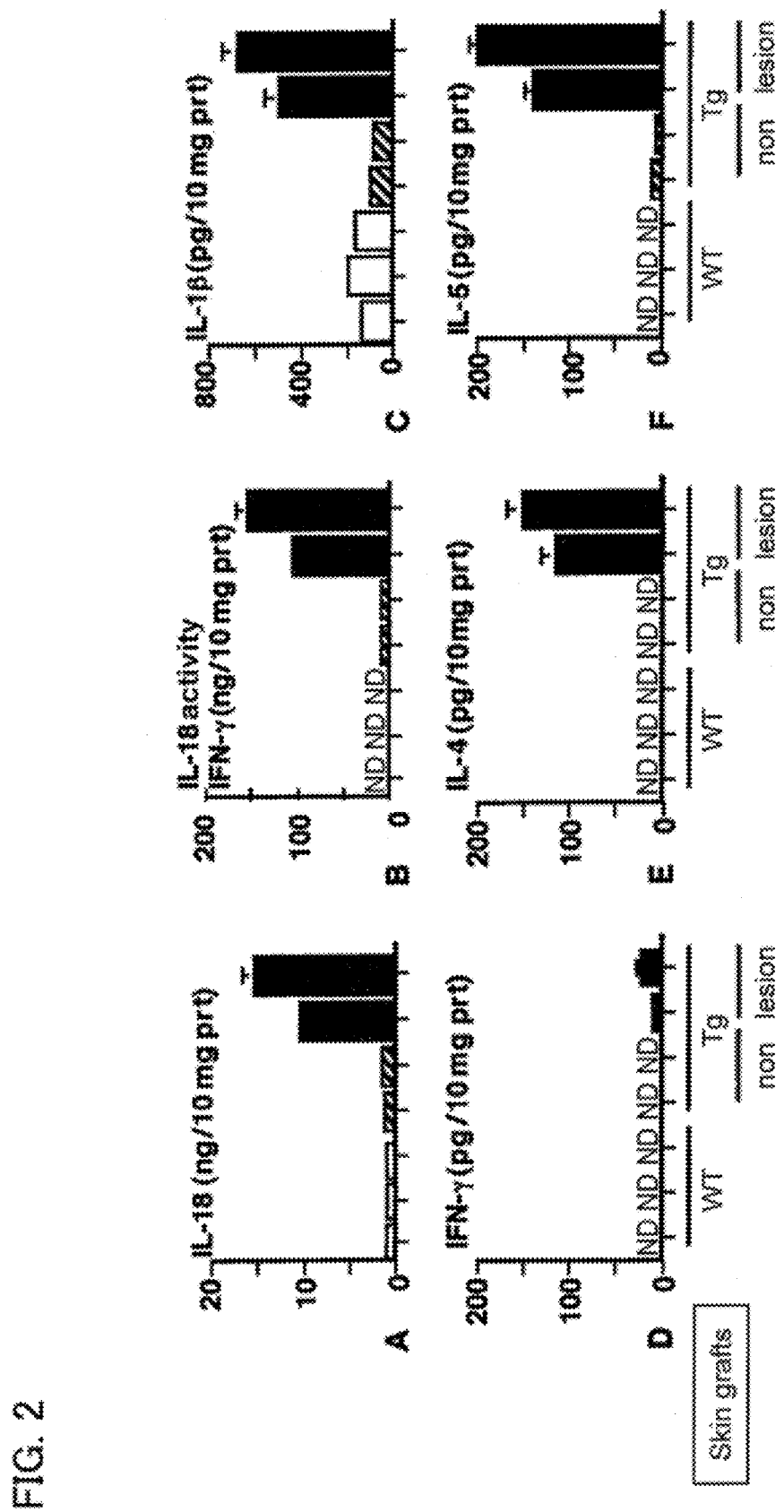
FIGS. 2A through 2F are views illustrating accumulation of IL-18 in lesion skin of KCASP1Tg mice, as well as the result of controls.

In FIGS. 2A through 2F, the closed block graph shows the result of a specimen of lesion skin sampled from two KCASP1Tg mice, the hatched block graph shows the result of a specimen of non-lesion skin sampled from two KCASP1Tg mice, and the open block graph shows the result of a skin specimen provided as a control sampled from three wild-type mice. Further, FIG. 2A illustrates concentration of IL-18 in lysates of each of the skin specimens, FIG. 2B illustrates activity of IL-18 (generation of IFN-γ by LNK5E6 cells having IL-18 responsiveness), FIG. 2C illustrates concentration of IL-1β, FIG. 2D illustrates concentration of IFN-γ, FIG. 2E illustrates concentration of IL-4, and FIG. 2F illustrates concentration of IL-5. Each result shows mean and standard deviation of three independent experimental results in each sample. Note that ND stands for "not detected".

As illustrated in FIG. 2A, the lysate of lesion skin of KCASP1Tg mice showed high levels of IL-18 measured by ELISA, and both precursor and matured forms of IL-18 were detected. On the other hand, the concentration of IL-18 was low in the lysate of non-lesion skin of KCASP1Tg mice, and lowest in the lysate of skin of wild-type mice.

Here, from immunoblotting analysis for IL-18, it is known that lesion portion of skin of KCASP1Tg mice expresses both bioactive IL-18 of 18 kDa and precursor IL-18 of 24 kDa, and that skin of wild-type mice and non-lesion skin of KCASP1Tg mice express only precursor IL-18 of 24 kDa. In order to confirm this, bioassay for IL-18 was performed. As a result, as illustrated in FIG. 2B, lesion skin of KCASP1Tg mice showed a high titer of IFN-γ-inducing activity of IL-18. On the other hand, non-lesion skin showed little activity. Further, normal skin of B6 mice had no such bioactive IL-18.

Further, as illustrated in FIG. 2C, IL-1β was concentrated in KC only in lesion skin. Note that it is known that, in addition to IL-18 and IL-1β, another product of caspase-1 was also concentrated in KC only in lesion skin. In this way, the IgE concentration in the hosts paralleled that of IL-18 and IL-1β levels in the transplanted graft.

Next, concentrations of IFN-γ, IL-4, and IL-5 in the lysate of lesion skin of KCASP1Tg mice were measured. As a result, as illustrated in FIGS. 2D through 2F, concentrations of IFN-γ, IL-4, and IL-5 in lysate of lesion skin of KCASP1Tg mice were all increased compared to lysates of non-lesion skin of wild-type mice and KCASP1Tg mice. In this way, the graft of lesion skin accumulated large amounts of IL-18, IL-1β, IFN-γ, IL-5, and IL-4.

In order to examine which type of cells are accumulated in the lesion skin of KCASP1Tg mice, proportions of CD4$^+$ T cells, CD8$^+$ T cells, and dendritic cells in KC specimens were measured by FACS. The results are illustrated in FIGS. 3A through 3F.

Figure 3:
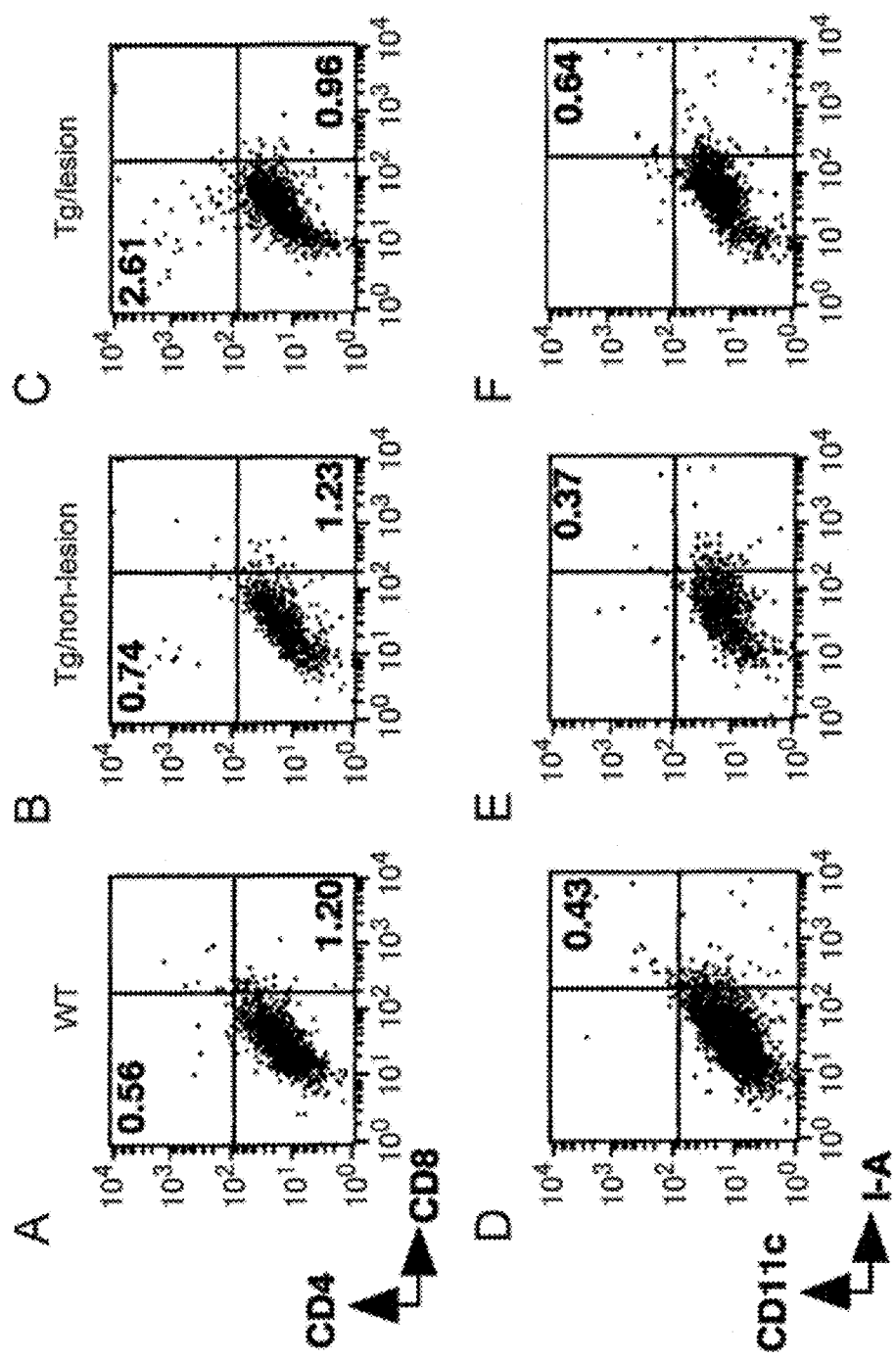
FIGS. 3A through 3F are views illustrating accumulation of CD4+ T cells in lesion skin of KCASP1Tg mice, as well as the results of controls.

FIGS. 3A and 3D illustrate the result of KC specimen obtained from normal skin of wild-type mice, FIGS. 3B and 3E illustrate the result of KC specimen obtained from non-lesion skin of KCASP1Tg mice, and FIGS. 3C and 3F illustrate the result of KC specimen obtained from lesion skin of KCASP1Tg mice.

FIGS. 3A through 3C are the results of incubating each KC specimen with PE-conjugated anti-CD4 antibody and FITC-conjugated anti-CD8 antibody. FIGS. 3D through 3F illustrate the results of incubating each KC specimen with PE-conjugated anti-CD 11c antibody and FITC-conjugated anti-I-A$^b$ antibody. Further, each of FIGS. 3A through 3F illustrate proportions of CD4$^+$ T cells and CD8$^+$ T cells, and proportions of CD 11c$^+$DC and I-A$^{b+}$ DC. Each result shows only the result of one mouse out of three mice in each experimental group.

As illustrated in FIGS. 3A through 3F, in the lesion skin, the number of CD4$^+$ T cells was substantially increased, compared to wild-type mice. Further, among these three types of recipients, there was no difference in the proportions of CD8$^+$ T cells or DC.

The number of mast cells was remarkably increased in the lesion skin, but not increased in the non-lesion skin, of KCASP1Tg mice, compared to wild-type mice (data is not shown). This result conforms to the previous report (Non-Patent Document 4) by the inventors of the present invention. In this way, CD4$^+$ T cells are preferentially accumulated in the lesion skin of KCASP1Tg mice. Further, a lot of mast cells are accumulated in the lesion skin.

EXAMPLE 3

Induction of Th1 Cells and Th2 Cells in Mice Transplanted with Lesion Skin

Because IgE response usually requires activation of Th2 cells, it was next examined whether CD4$^+$ T cells in the host develop into Th2 cells after transplantation of lesion skin. To be specific, lesion skin and non-lesion skin of KCASP1Tg mice and normal skin of wild-type mice were transplanted onto normal B6 mice, and 21 days later, their splenic CD4$^+$ T cells were incubated with immobilized anti-CD 3 for 48 hours, and IL 4 concentration (closed block graph) and IFN-γ concentration (open block graph) were determined by ELISA. The result is illustrated in FIG. 4.

Figure 4:
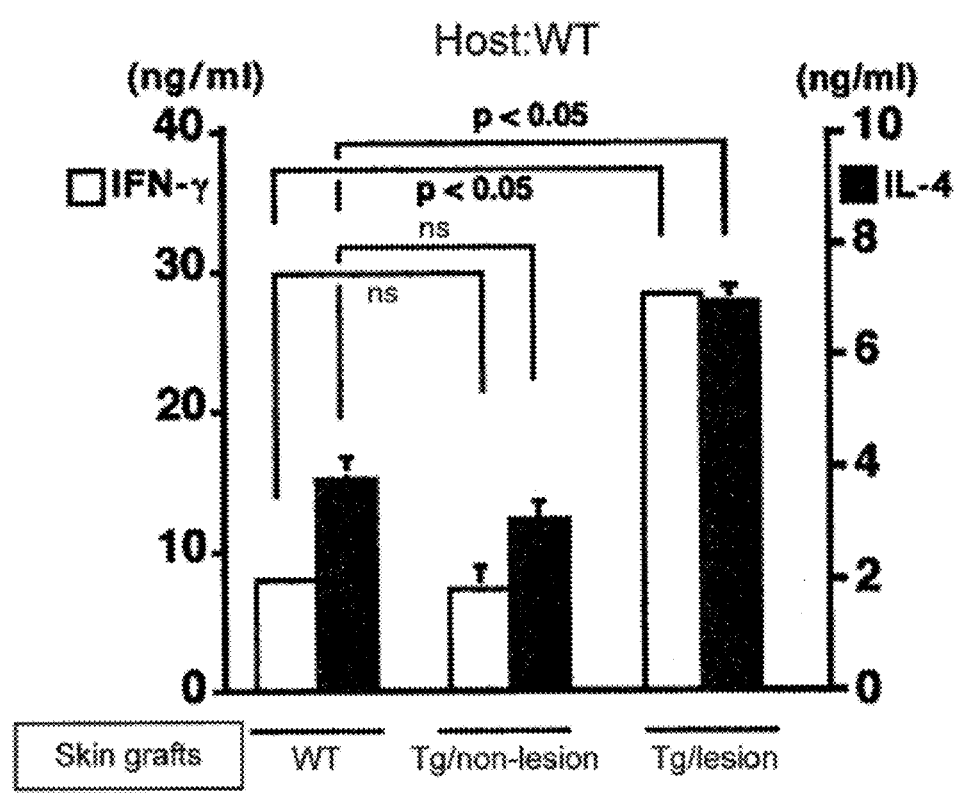
FIG. 4 is a view illustrating absence of selective Th2 cell differentiation in hosts transplanted with lesion skin, as well as illustrating the result of a control.

In FIG. 4, IL-4 concentration is illustrated by the closed block graph, and IFN-γ concentration is illustrated by the open block graph. Each data indicates mean and standard deviation of three sets. A similar result was obtained from the three independent experiments. Note that NS stands for "not significant".

As illustrated in FIG. 4, splenic CD4$^+$ T cells from hosts 21 days after transplantation of lesion skin of KCASP1Tg mice produced larger amounts of both IL-4 and IFN-γ in response to immobilized anti-CD3, compared to hosts transplanted with skin of normal B6 mice.

On the other hand, splenic CD4$^+$ T cells of recipients transplanted with non-lesion skin produced comparable amounts of IL-4 and IFN-γ as those from recipients transplanted with skin of B6 wild-type mice (response to plate-bound anti-CD3). However, 7 days after the implantation, CD4$^+$ T cells from the recipients transplanted with lesion skin or non-lesion skin of KCASP1Tg mice secreted comparable amounts of IL-4 and IFN-γ as those of CD4$^+$ T cells from control recipients transplanted with normal skin of wild-type mice (data is not shown).

These results show that it takes 2-3 weeks for CD4$^+$ T cells to develop into Th1/Th2 cells after stimulation by transplantation of the graft of lesion skin.

EXAMPLE 4

IL-18-, CD 4-, and Stat6-dependent IgE Induction

The cellular mechanism by which lesion skin of KCASP1Tg mice induces IgE was analyzed. It is known that CD4$^+$ T cell-depleted mice do not show any elevation of serum levels of IgE, even when IL-18 is administered to the mice. Therefore, it was examined whether host-derived CD4$^+$ T cells are essentially required, or IL-4 producing donor T cells (see FIG. 2E) which infiltrate lesion skin are equipped with conditions necessary for IgE induction.

Figure 5:
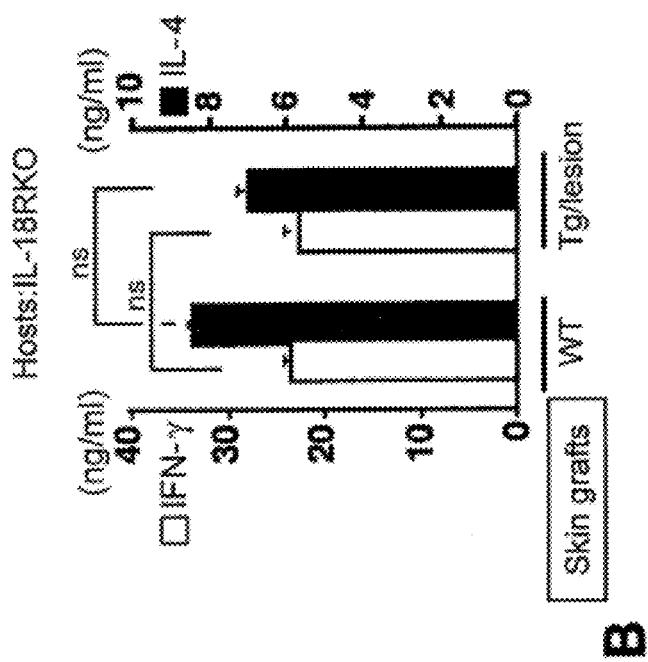
FIGS. 5A and 5b are views illustrating the results of host CD4+ T cells, host stat6 and host IL-18 responsiveness for IgE induction, and Th1/Th2 cell differentiation, as well as the results of controls.
Figure 5:
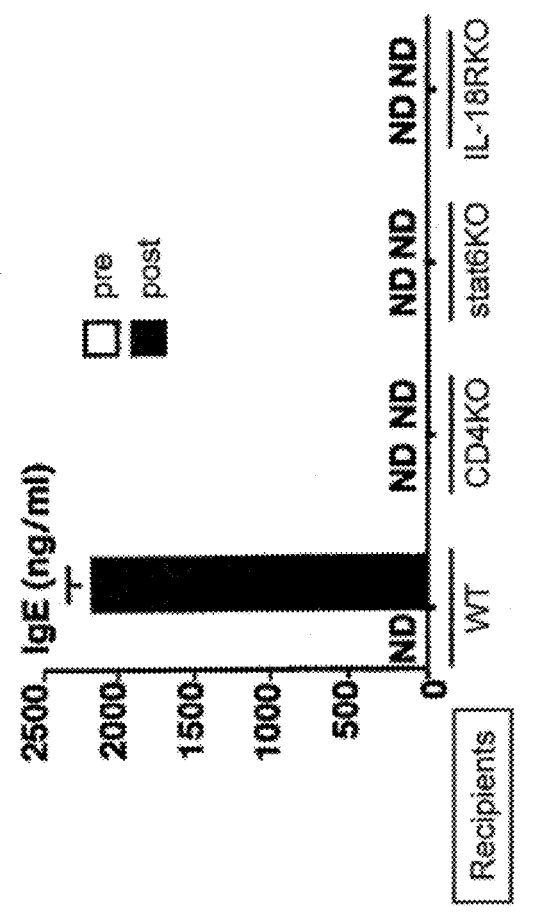

To be specific, lesion skin of KCASP1Tg mice were transplanted onto wild-type mice, CD4-deficient mice, stat6-deficient mice or IL-18 Rα-deficient mice. On day 0 and day 21, serum was sampled for measurement of IgE. The result of the measurement is illustrated in FIG. 5A. In FIG. 5A, the open block graph shows the result of the 0th day, and the closed block graph shows the result of the 21st day. Each data indicates mean and standard deviation of three mice in each experimental group.

First, as illustrated in FIG. 5A, CD4-deficient mice did not produce IgE even after transplantation with lesion skin of KCASP1Tg mice. This result suggests that, without host CD4$^+$ T cells, IL-4 producing cells or IL-18 in the skin graft of KCASP1Tg mice cannot induce systemic elevation of IgE.

Further, because stat6 is essential to signal transmission of IL-4, it was next examined whether activation of host-derived stat6 is critical to IgE induction. As illustrated in FIG. 5A, the result of the examination shows that stat6-deficient mice show no elevation of IgE after transplantation of lesion skin. The result suggests that IgE response induced by the graft of lesion skin depends on host-derived CD4$^+$ T cells and stat6. Transplantation with normal skin of B6 mice also did not induce production of IgE in hosts whose CD4$^+$ T cells or stat6 were deficient (data is not shown). Therefore, IgE induction caused by transplantation with skin occurs only when the host has intact CD4$^+$ T cells and stat6.

Further, it was examined whether IL-18 in the graft induces IgE in the host or not. For this purpose, IL-18Rα-deficient mice that cannot respond to IL-18 were used as hosts. As illustrated in FIG. 5A, IL-18Rα-deficient mice did not show increase in IgE. Further, IL-18Rα-deficient mice transplanted with normal skin of B6 mice did not show increase in IgE (data is not shown).

Taken together, these results show that persistent accumulation of a small amount of IL-18 in a lesion portion of skin induces systemic increase in IgE depending on host-derived CD4$^+$ T cells and stat6.

Further, because wild-type mice transplanted with lesion skin showed IgE response accompanied by differentiation of CD4$^+$ T cells to Th1 cells and Th2 cells (see FIG. 4), it was examined whether this differentiation to Th1/Th2 cells depends on endogenous IL-18 in the graft of lesion skin.

To be specific, normal skin of B6 wild-type mice or lesion skin of KCASP1Tg mice was transplanted onto IL-18Rα-deficient mice. On the day 21, splenic CD4$^+$ T cells was isolated from a recipient and stimulated with immobilized anti-CD3, and produced IL-4 and IFN-γ were measured by ELISA. The result of the measurement is illustrated in FIG. 5B.

In FIG. 5B, the open block graph indicates the result of IFN-γ and the closed block graph indicates the result of IL-4. Each data indicates mean and standard deviation of three mice in each experimental group. Note that NS stands for "not significant".

As illustrated in FIG. 5B, CD4$^+$ T cells from IL-18Rα-deficient mice transplanted with the graft of lesion skin did not differ, in terms of output of IL-4 or IFN-γ, from CD4$^+$ T cells from IL-18Rα-deficient mice transplanted with normal skin of wild-type mice. This result shows that differentiation to Th1/Th2 cells mediated by the graft of lesion skin depends on IL-18 released from the graft.

EXAMPLE 5

SpA Induction of IL-18 and IgE In Vivo

It is known that infection of *Staphylococcus aureus* occasionally exacerbates cutaneous inflammatory changes in patients with AD, and some patients with AD showed increased serum levels of IL-18. Therefore, it was examined whether products of *Staphylococcus aureus* causes systemic increase in IL-18 in normal B6 mice.

To be specific, various amounts of SpA or only vehicles were applied on ear skin of normal B6 mice once a day for two weeks. After that, on day 14, serum and spleens were sampled so as to measure concentration of IL-18 or IgE. Further, splenic CD4$^+$ T cells from mice on which vehicle or SpA(100 μg/day) was applied were incubated with plate-bound anti-CD3 for 48 hours, and concentrations of IFN-γ and IL-4 in each supernatant were measured by ELISA. The results of the measurements are illustrated in FIGS. 6A through 6C.

Figure 6:
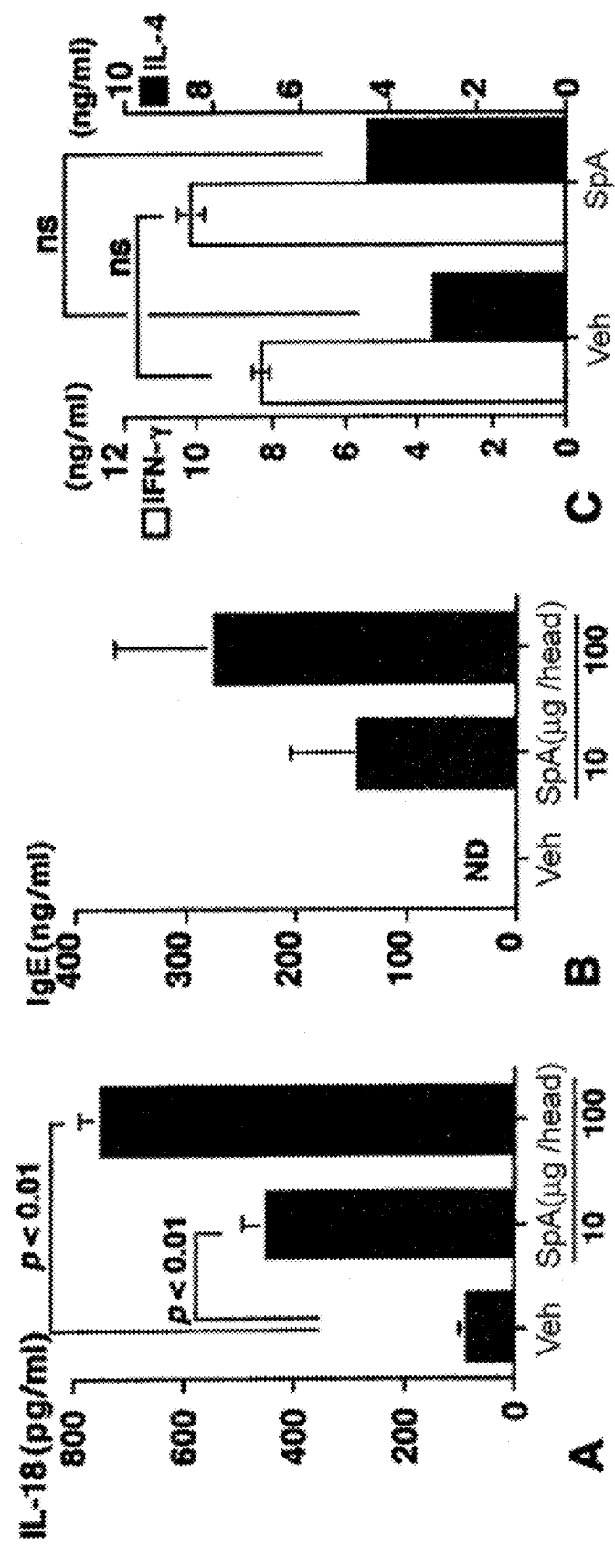
FIGS. 6A through 6C are views illustrating the results of induction of IL-18 and IgE by in vivo treatment with SpA, as well as the results of controls.

FIG. 6A illustrates the result of IL-18, and FIG. 6B illustrates the result of IgE. Further, the open block graph in FIG. 6C illustrates the result of IFN-γ, and the closed block graph illustrates the result of IL-4. Data of FIGS. 6A and 6B indicate mean and standard deviation of three mice in each group. Data of FIG. 6C indicates mean and standard deviation of three samples, and indicates data of one mouse out of three mice in each group. Note that ND stands for "not detected", and NS stands for "not significant".

As illustrated in FIG. 6A, serum levels of IL-18 increased in mice on which SpA was applied in a dose-dependent manner, but not in mice on which only vehicle was applied. IL-12p40 and IL-12p70 in sera of mice on which SpA or vehicle was applied were not detected by ELISA (data is not shown). Further, as illustrated in FIG. 6B, IgE levels were also increased in a dose-dependent manner. Besides, as illustrated in FIG. 6C, mice treated with SpA did not show preferential differentiation of Th2 cells. These results show that, as with the treatment of IL-18, SpA has the potential to induce systemic IgE without preferential differentiation of Th1 cells or Th2 cells.

EXAMPLE 6

KC Secrete IL-18, but not IL-12, in Response to SpA

IL-18 without IL-12 is capable of inducing IgE, while IL-18 with IL-i2 inversely inhibits IgE induction. It is known that the stimuli including LPS (lypopolysaccharide) which induce IL-18 secretion always cause IL-12 production. Therefore, it was next examined what type of cells secrete IL-18, and whether the cells secrete without accompanied by production of IL-12 in response to SpA.

Figure 7:
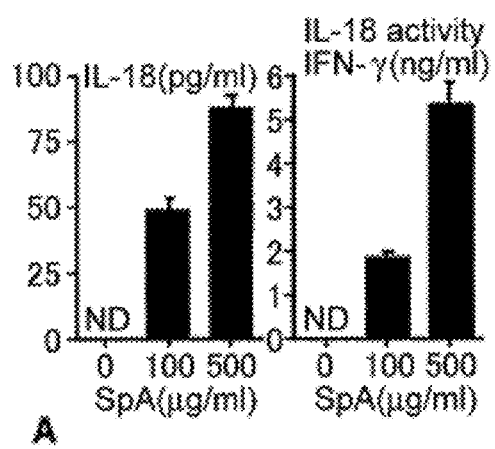
FIGS. 7A through 7D are views illustrating the results that not IL-12 but IL-18 is released from SpA-stimulated KC, as well as the results of controls.
Figure 7:
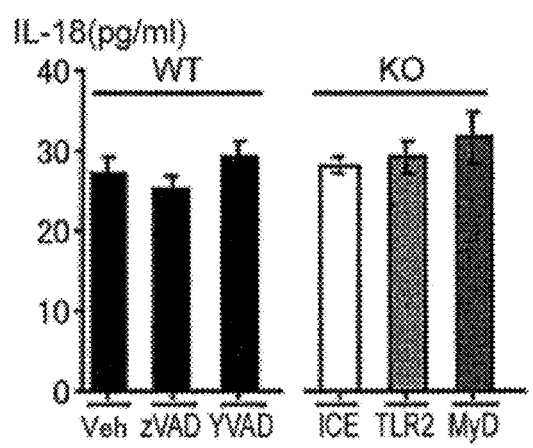
Figure 7:
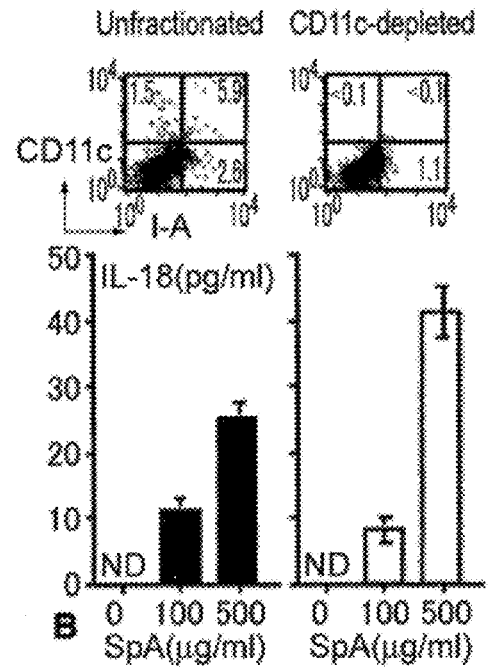
Figure 7:
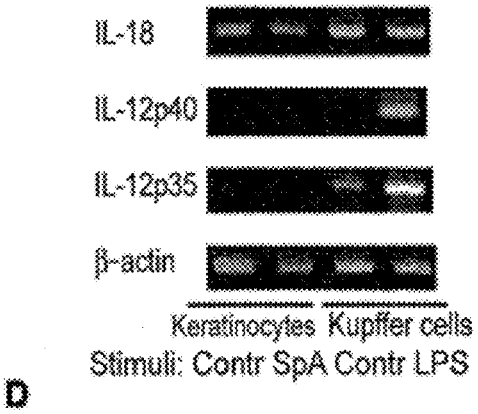

To be specific, PAM212 cells (culture strain of KC of mice) were incubated with or without SpA for 24 hours, and the IL-18 concentration and IFN-γ-inducing bioactivity of IL-18 in each supernatant were determined by ELISA and bioassay respectively. The result of the measurement is illustrated in FIG. 7A. In FIG. 7A, the left side illustrates the IL-18 concentration, and the right side illustrates the IFN-γ-inducing activity. Note that data of FIG. 7A indicates mean and standard deviation of three values. ND stands for "not detected".

As is evident from FIG. 7A, after stimulation with SpA, PAM212 cells secreted activated IL-18 which can induce production of IFN-γ.

Further, in order to examine whether newly isolated KC secrete IL-18 in response to SpA, KC from wild-type B6 mice were incubated with various amounts of SpA for 24 hours.

To be specific, KC or CD11c$^+$ cell-depleted KC prepared from skin of wild-type B6 mice were analyzed for their expression of CD11c and MHC class II (1-A$^b$) by flow cytometry. These cells were incubated with or without SpA for 24 hours, and concentration of IL-18 in the resulting supernatant was measured by ELISA. The result of the measurement is illustrated in FIG. 7B. In FIG. 7B, the KC prepared from skin of wild-type B6 mice are illustrated by the closed block graph, and the CD11c$^+$ cell-depleted KC are illustrated by the open block graph.

As illustrated in the left side of FIG. 7B, in response to SpA, the newly isolated KC released IL-18 in a dose-dependent manner. Because LC/DC can release IL-18, CD11c$^+$ cells were removed from KC specimens, and the KC specimens were incubated with SpA. As illustrated in the right side of FIG. 7B, even after CD11c$^+$ cells were removed, the KC secreted IL-18 in response to stimulation with SpA. Note that data of FIG. 7B indicates mean and standard deviation of three values. ND stands for "not detected".

Next, the molecular mechanisms underlying SpA-induced IL-18 secretion from KC were examined. Because caspase-1 is required for LPS (lypopolysaccharide)-induced IL-18 secretion, IL-18 secretion from SpA-stimulated caspase-1-deficient KC was examined.

To be specific, KC were prepared from wild-type mice, caspase-1-deficient mice, TLR2-deficient mice, or MyD88-deficient mice. The KC of the wild-type mice were incubated with 500 μg/ml SpA in the presence of 20μ MZVAD, 20 μM YVAD, or the same volume of DMSO(Veh) for 24 hours. On the other hand, KC from each of the mutants were incubated with 500 μg/ml SpA for 24 hours. IL-18 in each supernatant was measured by ELISA. The result is illustrated in FIG. 7C.

In FIG. 7C, WT indicates wild-type mice, and KO indicates each of the mutants (knock out type) mice, and the open block graph indicates caspase-1-deficient mice, the hatching block graph indicates TLR2-deficient mice, and the block graph formed by oblique lines indicates MyD88-deficient mice.

As illustrated in FIG. 7C, KC of wild-type mice incubated with 500 μg/ml SpA without adding DMSO produced 28.4±3.5 pg/ml of IL-18. Further, KC of caspase-1-deficient mice secreted comparable levels of IL-18 as KC of wild-type mice. This suggests that IL-18 is secreted independently of caspase-1, in response to SpA. Note that data of FIG. 7C indicates mean and standard deviation of three values.

YVAD which is a caspase-1 inhibitor, and ZVAD which is a broad caspase inhibitor, strongly inhibit secretion of IL-18 from Kupffer cells which are tissue macrophage in a liver, the secretion being caused by LPS or membrane-bound Fas ligand stimulation. For that reason, it was examined whether IL-18 secretion from SpA-stimulated KC is influenced by YVAD or ZVAD. As illustrated in FIG. 7C, these two types of caspase inhibitors did not inhibit secretion of IL-18 from KC of wild-type mice stimulated with SpA. The result shows that caspase is unnecessary in IL-18 secretion from KC stimulated with SpA. The same is applied to KC of caspase-1-deficient mice (data is not shown).

Further, because many microbes stimulate TLR/MyD88 signaling pathways, it was examined whether KC secrete IL-18 depending on TRL2 which is a signaling receptor for Gram-positive bacteria, or on MyD88 which is indispensable adaptor molecule shared by all TRL members. As illustrated in FIG. 7C, both TLR2 and MyD88 are unnecessary for IL-18 secretion from KC induced by SpA stimulation, which suggests that IL-18 secretion induced by SpA does not depend on TLR.

Further, because Kupffer cells secrete IL-18 in response to stimulation with LPS or membrane-bound Fas ligand, it was examined whether these stimuli induce IL-18 secretion from KC. To be specific, KC ($5 \times 10^5$/ml) from wild-type B6 mice were incubated with 500 µg/ml SpA, 1 µg/ml LPS, or $1 \times 10^6$/ml mFasL for 24 hours. IL-18 contained in each resulting supernatant was measured by ELISA. The result of the measurement is shown in Table 1.

TABLE 1

| | stimulator | | | |
|---|---|---|---|---|
| | Only culture solution | SpA | LPS | mFasL |
| IL-18(pg/ml) | ND | 31.5 ± 3.2 | ND | ND |

As is evident from the result of Table 1, contrary to Kupffer cells, KC did not secrete IL-18 even after being stimulated with LPS or Fas ligand. Note that ND stands for "not detected" in Table 1.

Next, it was examined whether SpA-stimulated KC secretes IL-12 as well as IL-18. In order to detect a small amount of IL-12, total RNA were obtained from KC that had been incubated with SpA for 4 hours, and RT-PCR was performed using the RNA. To be specific, KC and Kupffer cells of wild-type B6 mice were separately incubated in the presence/absence of 500 µg/ml SpA, and in the presence/absence of 1 µg/ml LPS for 4 hours. Expression level of mRNA of IL-18, IL-12p40, IL-12p35, and β-actin out of all extracted RNA were measured by RT-PCR. The result of the measurement is illustrated in FIG. 7D.

As illustrated in FIG. 7D, Kuppfer cells stimulated with LPS expressed both IL-12p35 and IL-12p40. On the other hand, in KC stimulated with SpA, neither IL-12p35 nor IL-12p40 were detected. RT-PCR for IL-12 was performed using total RNA from KC having been incubated with SpA for 8 or 16 hours, but any kind of IL-12 was detected in the RNA. IL-12 was measured also by ELISA, but IL-12p40 or IL-12p70 was not detected in supernatant of KC stimulated with SpA after 24-hour incubation (data is not shown).

On the other hand, KC of Kupffer cells constitutively expressed IL-18, and did not change expression level after stimulation with SpA. Further, Kupffer cells did not secrete IL-12 or IL-18 in response to SpA (data is not shown).

These results show that SpA applied to skin stimulates the local KC to secrete IL-18, but not IL-12, leading to induction of IgE.

EXAMPLE 7

Skin Lesion of NC/Nga Mice on Which Mixture of SDS and SpA was Applied

NC/Nga mice are atopic dermatitis favorite mice, and do not develop AD under specific pathogen-free SPF, but develop AD under a conventional environment. When either 4% of SDS or SpA (200 µg/day) is applied, NC/Nga mice do not develop AD. However, when a mixture of SDS and SpA is applied on shaven backs of NC/Nga mice, a skin lesion like AD is observed.

Figure 8:
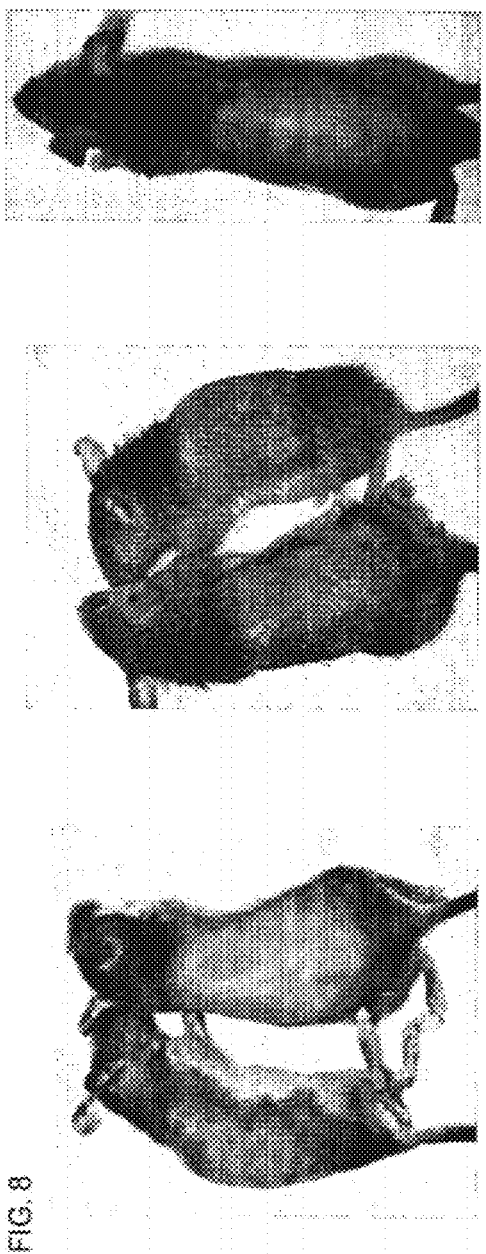
FIGS. 8A through 8D are views illustrating the results of a skin lesion of NC/Nga mice on which mixture of 4% SDS and SpA (200 µg/day) is applied, as well as the results of controls.
Figure 8:

FIGS. 8A through 8D are views illustrating the result of a skin lesion of NC/Nga mice on which mixture of 4% of SDS and SpA (200 µg/day) was applied, as well as the result of controls. As illustrated in FIG. 8C, when 4% of SDS was solely applied, no development of AD was observed 28 days later. However, as illustrated in FIGS. 8B and 8D, when the mixture of 4% of SDS and SpA (200 µg/day) was painted, skin lesion like AD was observed 14 days later and 28 days later.

FIGS. 9A through 9D show changes in the skin of the NC/Nga mice on which the mixture of 4% SDS and SpA (200 µg/day) was applied, as well as changes in the skin of the controls. FIGS. 9A through 9C show the result of observation by an optical microscope of lesion skin like AD stained with hematoxylin eosin. FIG. 9A shows the result of observation with 25 magnifications, FIG. 9B shows the result of observation with 50 magnifications, and FIG. 9C shows the result of observation with 100 magnifications. FIG. 9D shows the result of observation by an optical microscope of Alcian blue-stained lesion skin like AD. As illustrated in FIG. 9D, histologically, thickening of epidermis became evident at a diseased portion, and infiltration of mast cells stained with Alcian blue was observed.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

As described above, the present invention is a method of screening, a method of inducing atopic dermatitis-like symptom, and usages thereof, based on the finding that local accumulation of IL-18 from KC causes systemic IgE response without exposure to an antigen, resulting in high-level IgE in serum in an inflammatory skin lesion like AD.

Therefore, the present invention shows significance of production of IL-18 from KC induced by stimulation with microbes, provides a new knowledge to a mechanism which may be related to a cause of an allergic disease due to an unknown antigen, and can be effectively used for development of therapeutic drugs and the like for AD.

Therefore, the present invention can be applied to medical fields, as well as to drug industries and investigative reagent industries. As such, the present invention shows significance of the production of IL-18 from KC caused by stimulation with microbes, provides a new knowledge to a mechanism which may be related to a cause of an allergic disease due to an unknown antigen, and can be effectively used for development of therapeutic drugs and the like for AD.

The invention claimed is:

1. A method for screening for an inhibitor which inhibits induction of production of interleukin 18 from keratinocytes, said method comprising: a step for inducing the production of interleukin 18 from keratinocytes, by applying a stimulator on the skin of a normal living organism provided as a host thereby producing an interleukin 18 mediated inflammation;

and an inhibitor identifying step for applying a candidate-substance on the inflammatory part of the living organism to which the stimulator has been applied, or orally administering the candidate-substance to the living organism to which the stimulator has been applied, and identifying, as the inhibitor, a substance which inhibits the induction of the production of interleukin 18 from the keratinocytes, the stimulator being selected from at least one of (i) protein A derived from *Staphylococcus aureus* or (ii) a mutant of the protein A, the mutant being capable of stimulating keratinocyte being used, and the mutant being a protein which (i) has an amino acid sequence with amino acids, the number of which is not less than 1 but not more than 5, replaced, deleted, inserted, and/or added, and (ii) negatively controls expression of B7-2 molecule of a surface of cells.

2. The method as set forth in claim 1, wherein, as the stimulator, SDS as well as protein A is used.

3. The method as set forth in claim 1, wherein the living organism provided as the host is a mouse.

4. The method as set forth in claim 1, wherein the stimulator is the protein A derived from *Staphylococcus aureus*.

5. A method for screening for an inhibitor which inhibits induction of production of interleukin 18 from keratinocytes, said method comprising:

a step for inducing the production of interleukin 18 from keratinocytes by using, as the stimulator, a skin graft on which an inflammatory skin lesion like atopic dermatitis is developed, and transplanting the skin graft onto the skin of a living organism provided as a host thereby producing an interleukin 18 mediated inflammation;

and an inhibitor identifying step for applying a candidate-substance on the inflammatory part of the living organism provided as the host, or orally administering the candidate-substance to the living organism provided as the host, and identifying, as the inhibitor, a substance which inhibits the induction of the production of interleukin 18 from the keratinocytes, the living organism provided as the host being at least such that (i) $CD4^+T$ cells normally exist, (ii) stat6 is expressed, and (iii) NKT cells constitutively express IL-18R$\alpha$ chain.

6. The method as set forth in claim 5, wherein the living organism provided as the host is a mouse.

* * * * *